(12) United States Patent
Connelly et al.

(10) Patent No.: US 6,416,502 B1
(45) Date of Patent: Jul. 9, 2002

(54) ABSORBENT ARTICLE HAVING CHANNELS FOR RECEIVING THE EDGES OF AN UNDERGARMENT

(75) Inventors: Thomas John Connelly, Appleton; Joyce Ann Damico, Neenah; Gary Chester Anderson, Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/054,981

(22) Filed: Apr. 3, 1998

(51) Int. Cl.$^7$ .................................................. A61F 13/15

(52) U.S. Cl. .................. 604/387; 604/385.04; 604/386; 604/389; 604/385.01

(58) Field of Search ................................ 604/379, 380, 604/382, 383, 385.01, 385.03, 385.04, 385.05, 385.11, 385.14, 385.2, 386, 387, 367, 378, 385.23, 385.24, 389, 393, 397, 398

(56) References Cited

U.S. PATENT DOCUMENTS

| | | | |
|---|---|---|---|
| 2,787,271 A | 4/1957 | Clark .......................... 128/290 |
| 4,031,897 A | 6/1977 | Graetz ......................... 128/286 |
| 4,184,498 A | 1/1980 | Franco .................... 128/290 R |
| 4,285,343 A | 8/1981 | McNair ....................... 128/287 |
| 4,475,913 A | 10/1984 | Hlaban |
| 4,526,825 A | 7/1985 | Whitehead ..................... 428/74 |
| 4,559,051 A | 12/1985 | Hanson .................. 604/385 R |
| 4,578,066 A | 3/1986 | O'Connor .................... 604/366 |
| 4,589,876 A | * 5/1986 | Van Tilburg ................. 604/385 |
| 4,610,679 A | 9/1986 | Matsushita .................. 604/369 |
| 4,655,759 A | 4/1987 | Romans-Hess et al. . 604/385 R |
| 4,675,016 A | 6/1987 | Meuli et al. ............. 604/385 A |
| 4,687,478 A | 8/1987 | Van Tilburg ................. 604/387 |
| 4,701,177 A | 10/1987 | Ellis et al. ............... 604/385 A |
| 4,701,178 A | * 10/1987 | Gluag et al. ................. 604/387 |
| 4,753,644 A | 6/1988 | Cottenden et al. .......... 604/378 |
| 4,753,645 A | 6/1988 | Johnson ...................... 604/378 |
| 4,758,240 A | * 7/1988 | Glassman .................... 604/379 |
| 4,773,904 A | 9/1988 | Nakanishi et al. .......... 604/372 |
| 4,790,839 A | 12/1988 | Ahr ............................. 604/367 |
| 4,828,555 A | 5/1989 | Hermansson ............... 606/379 |
| 4,834,740 A | 5/1989 | Suzuki et al. ............ 604/385.2 |
| 4,846,823 A | 7/1989 | Enloe ...................... 604/385.2 |

(List continued on next page.)

FOREIGN PATENT DOCUMENTS

| | | | | |
|---|---|---|---|---|
| CA | 2079150 A1 | 3/1993 | | |
| EP | 0 496 709 A1 | 7/1992 | | |
| FR | 1553982 A1 | 12/1967 | | |
| JP | 63-186425 U | 11/1988 | ........... A61F/13/18 |
| JP | 63-186425 U | 11/1988 | | |

Primary Examiner—John G. Weiss
Assistant Examiner—Michele Kidwell
(74) Attorney, Agent, or Firm—Thomas M. Parker

(57) ABSTRACT

An absorbent article is disclosed which is designed to be secured to an undergarment. The undergarment includes a crotch protion with a pair of side edges. The absorbent article includes a liquid permeable cover, a liquid-impermeable baffle and an absorbent enclosed by the cover and the baffle to form a pad. The pad has first and second raised longitudinally-extending sides, each with a vertically oriented outer surface. The pad also has a garment-facing surface. The absorbent article also includes a pair of flaps which cooperate with one another to extend around the crotch portion of the undergarment and overlap one another. Each of the flaps has a proximal edge and a distal edge. The proximal edges are affixed to one of the vertically oriented outer surfaces and each of the distal edges extend downwardly and inwardly around the crotch portion of the undergarment. The pair of flaps are secured together by an attachment. The absorbent article further includes first and second channels formed in the garment-facing surface of the pad. The first and second channels are sized and configured to mate with the side edges of the undergarment.

6 Claims, 11 Drawing Sheets

U.S. PATENT DOCUMENTS

| | | | |
|---|---|---|---|
| 4,946,454 A | | 8/1990 | Schmidt ................... 604/385.1 |
| 5,009,651 A | | 4/1991 | Kamishioiri et al. ........ 604/378 |
| 5,030,229 A | | 7/1991 | Yang ....................... 604/385.1 |
| 5,074,856 A | | 12/1991 | Coe et al. ................. 604/385.1 |
| 5,133,705 A | | 7/1992 | Nakanishi et al. ........... 604/387 |
| 5,154,715 A | | 10/1992 | Van Iten ..................... 604/387 |
| 5,171,302 A | | 12/1992 | Buell ....................... 604/385.1 |
| 5,176,669 A | | 1/1993 | Klemp ....................... 604/387 |
| 5,197,959 A | | 3/1993 | Buell ....................... 604/385.1 |
| 5,211,641 A | | 5/1993 | Roos et al. ............... 604/385.1 |
| 5,221,275 A | | 6/1993 | Van Iten ..................... 604/387 |
| 5,234,422 A | | 8/1993 | Sneller et al. ............ 604/385.2 |
| 5,246,431 A | | 9/1993 | Minetola et al. .......... 604/385.2 |
| 5,267,992 A | | 12/1993 | Van Tilburg ................. 604/387 |
| 5,275,591 A | | 1/1994 | Mavinkurve |
| 5,300,056 A | | 4/1994 | Webb |
| 5,346,486 A | | 9/1994 | Osborn, III et al. ..... 604/385.1 |
| 5,366,453 A | | 11/1994 | Zehner et al. ............ 604/385.2 |
| 5,387,210 A | * | 2/1995 | Murakami ................. 604/396 |
| 5,389,094 A | | 2/1995 | Lavash et al. ............ 604/385.2 |
| 5,391,162 A | | 2/1995 | Widlund et al. .......... 604/385.2 |
| 5,413,569 A | | 5/1995 | Yamamoto ................ 604/385.2 |
| 5,447,507 A | * | 9/1995 | Yamamoto ................ 604/385.2 |
| 5,477,506 A | | 12/1995 | Lindquist .................... 604/374 |
| 5,489,283 A | | 2/1996 | Van Tillburg ................ 604/387 |
| 5,490,847 A | | 2/1996 | Correa et al. ............... 604/387 |
| 5,520,676 A | * | 5/1996 | Lavash et al. ............... 604/390 |
| 5,545,156 A | | 8/1996 | DiPalma et al. ......... 604/385.1 |
| 5,558,657 A | * | 9/1996 | Hammons et al. ..... 604/385.01 |
| 5,575,786 A | | 11/1996 | Osborn, III |
| 5,584,829 A | * | 12/1996 | Lavash et al. ............... 604/387 |
| 5,591,147 A | * | 1/1997 | Couture-Dorschner et al. ......................... 604/369 |
| 5,599,337 A | | 2/1997 | Mccoy .................... 604/385.1 |
| 5,620,430 A | | 4/1997 | Bamber |
| 5,628,739 A | * | 5/1997 | Hsieh et al. ............. 604/385.1 |
| 5,649,917 A | * | 7/1997 | Roberts et al. .......... 604/385.1 |
| 5,704,930 A | | 1/1998 | Lavash et al. |
| 5,713,886 A | | 2/1998 | Sturino |
| 5,795,344 A | * | 8/1998 | Chappell .................... 604/379 |
| 5,795,349 A | * | 8/1998 | Lavash et al. ............... 604/387 |
| 5,820,618 A | * | 10/1998 | Roberts et al. .......... 604/385.1 |
| 5,860,965 A | * | 1/1999 | Lavash et al. ............... 604/390 |
| 5,891,121 A | * | 4/1999 | Redwine et al. ............ 604/387 |
| 5,941,861 A | * | 8/1999 | Ng .............................. 604/366 |
| 5,951,536 A | * | 9/1999 | Osborn, III et al. ........ 604/387 |
| 5,951,537 A | | 9/1999 | Osborn, III |
| 5,972,806 A | * | 10/1999 | Weinberger et al. .......... 442/62 |
| 6,004,893 A | | 12/1999 | Van Tilburg |
| 6,007,528 A | | 12/1999 | Osborn, III |
| 6,059,763 A | | 5/2000 | Brown |
| 6,102,892 A | * | 8/2000 | Putzer et al. ................ 604/101 |

* cited by examiner

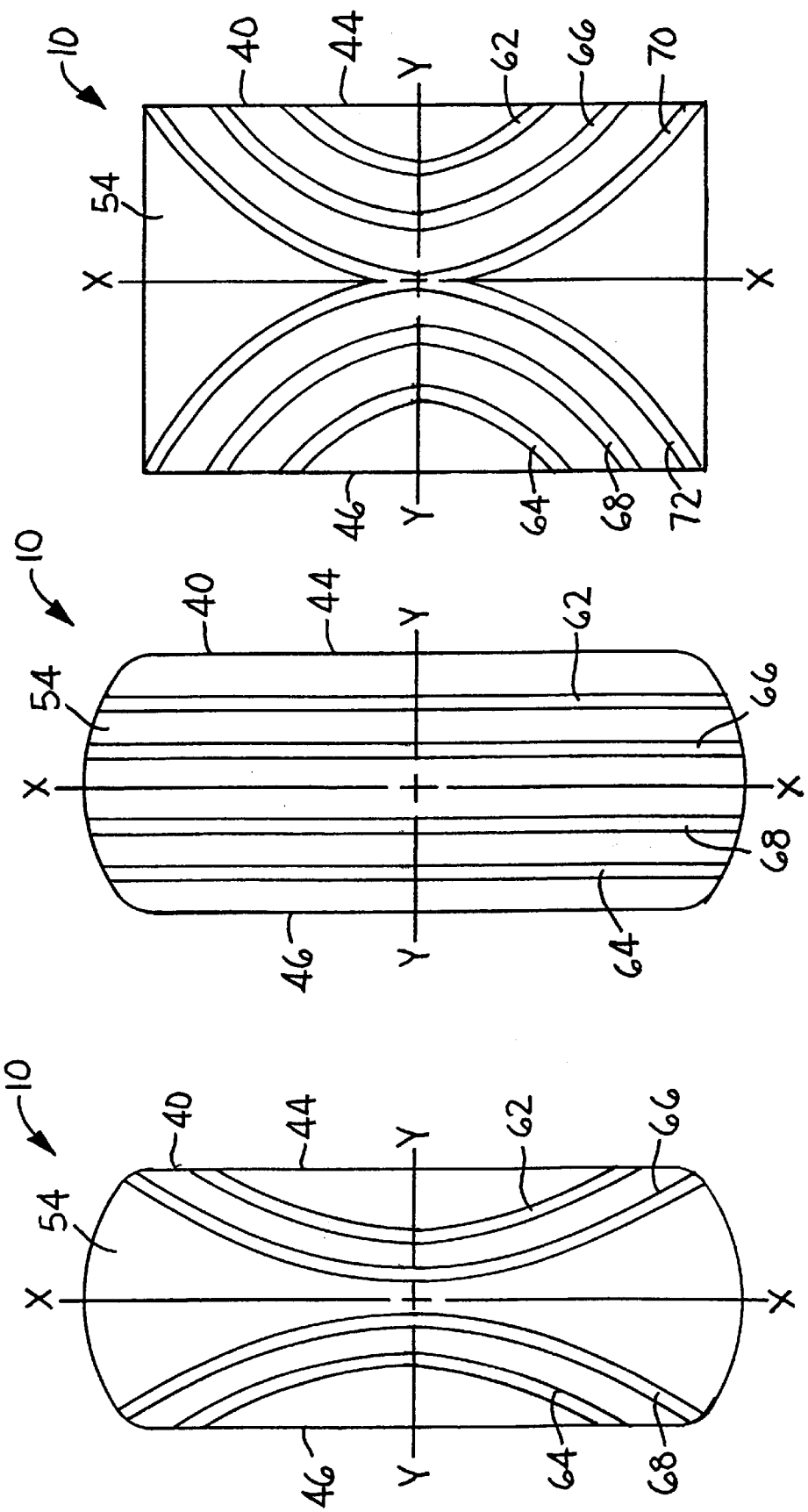

ABSORBENT ARTICLE HAVING CHANNELS FOR RECEIVING THE EDGES OF AN UNDERGARMENT

FIELD OF THE INVENTION

This invention relates to an absorbent article such as a sanitary napkin, pantyliner, incontinent garment, etc. More specifically, this invention relates to an absorbent article having a pair of raised longitudinally-extending sides, a pair of channels formed in its lower surface which are designed to receive the edges of an undergarment and a pair of flaps which extend downward and inward around the crotch portion of the undergarment.

BACKGROUND OF THE INVENTION

Absorbent articles, such as sanitary napkins, catamenial pads, feminine pads, pantyliners, incontinent garments and the like, are designed to be worn by humans to absorb discharged body fluid. Typical body fluids include urine, menstrual fluid, menses and perspiration. Such absorbent articles are classified as external devices which are generally held in position against the torso of a human body by a garment-attachment adhesive which is designed to be secured to the inner crotch portion of an undergarment. Other attachment methods include mechanical fasteners designed to secure the absorbent article to the undergarment or to another piece of clothing, such as a belt or girdle. Still other attachment methods include the use of one or more flaps or wings which are designed to wrap around the crotch portion of an undergarment and secure it thereto. Such products differ from tampons which are classified as internal devices and which are designed to be physically inserted into a female vagina. Functionally, sanitary napkins, catamenial pads and feminine pads are designed to absorb a greater quantity of body fluid and are made to be worn for longer periods of time than smaller external products such as pantyliners and panty shields.

In order to adequately perform their function, such absorbent articles should be positioned and retained close to the crotch region of the human body. The closer an absorbent article is held to or against the body, the better it is able to intercept discharged body fluid with less chance of leakage. It is therefore desirable to manufacture an absorbent article which contains a structure which will enable it to be securely held against the crotch region of the human body and to move with the body as the torso and thighs are manipulated and moved.

SUMMARY OF THE INVENTION

Briefly, this invention relates to an absorbent article designed to be secured to an undergarment. The undergarment includes a crotch protion with a pair of side edges. The absorbent article includes a liquid permeable cover, a liquid-impermeable baffle and an absorbent enclosed by the cover and the baffle to form a pad. The pad has first and second raised longitudinally-extending sides, each with a vertically oriented outer surface. The pad also has a garment-facing surface. The absorbent article also includes a pair of flaps which cooperate with one another to extend around the crotch portion of the undergarment and overlap one another. Each of the flaps has a proximal edge and a distal edge. The proximal edges are affixed to one of the vertically oriented outer surfaces and each of the distal edges extend downwardly and inwardly around the crotch portion of the undergarment. The pair of flaps are secured together by an attachment. The absorbent article further includes first and second channels formed in the garment-facing surface of the pad. The first and second channels are sized and configured to mate with the side edges of the undergarment.

The general object of this invention is to provide an absorbent article such as a sanitary napkin, a pantyliner, an incontinent garment, etc. which has a pair of downwardly and inwardly extending flaps to prevent staining of the adjacent undergarment and at least two grooves or channels formed in a lower surface of the absorbent article which are sized and configured to receive the edges of an undergarment. A more specific object of this invention is to provide an absorbent article which has a pair of raised longitudinally-extending sides which are sized to enter the groin of the user and prevent side leakage.

Another object of this invention is to provide an absorbent article which is easy to manufacture and is relatively low in cost.

A further object of this invention is to provide an absorbent article which functionally can minimize leakage of body fluids.

Still another object of this invention is to provide an absorbent article which has multiple grooves or channels formed in a lower surface thereof which provide alternative ways of engaging with the side edges of an undergarment.

Still further, an object of this invention is to provide an absorbent article which contains a structure which enables it to cooperate with an adjacent undergarment so that it can be securely maintained against the crotch region of a human body.

Other objects and advantages of the present invention will become more apparent to those skilled in the art in view of the following description and the accompanying drawings.

BRIEF DESCRIPTION OF THE DRAWINGS

FIG. 20 is a bottom view of an absorbent article having a multiple number of non-linear grooves or channels formed therein.

FIG. 21 is a bottom view of an absorbent article having a multiple number of linear grooves or channels formed therein.

FIG. 22 is a bottom view of an absorbent article having a multiple number of non-linear grooves or channels formed therein.

DETAILED DESCRIPTION OF THE PREFERRED EMBODIMENT

Figure 1:
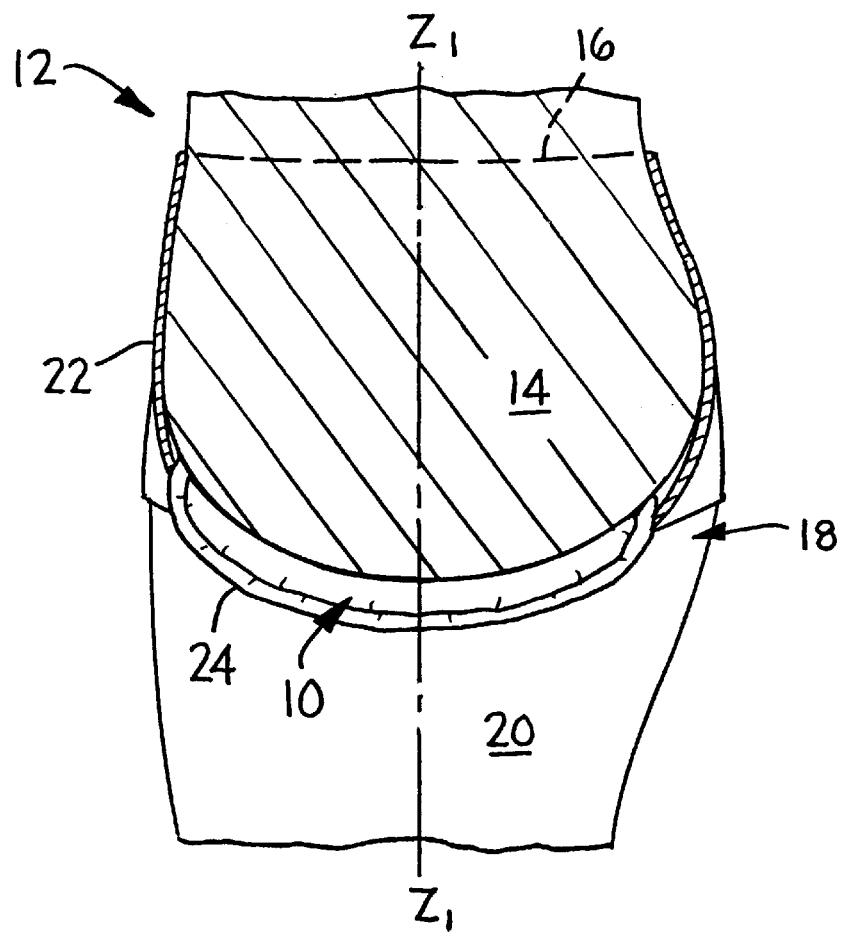
FIG. 1 is a schematic side view of a human torso sliced vertically in half and shows an absorbent article retained adjacent to the crotch region by an undergarment.

Referring to FIG. 1, an absorbent article 10 is shown positioned adjacent to the crotch region of a human body 12. The absorbent article 10 can be a sanitary napkin, a catamenial pad, a feminine pad, a pantyliner, a panty shield, an incontinent garment, or some other type of absorbent product. For purposes of discussion, the absorbent article 10 will be described as a sanitary napkin. The sanitary napkin 10 is designed to be worn by women to absorb discharged body fluid, especially menstrual fluid and urine. In FIG. 1, a side view of a human body 12 is shown which includes a torso 14 having a waist 16 and a crotch region 18 located at a lower end of the torso. A pair of legs 20 depend downward from the crotch region 18, one of which is shown. The sanitary napkin 10 is retained in close proximity to the pudendum or vulva area of a woman by an undergarment 22. The undergarment 22 is a typical pair of underpants having a waist opening, two leg openings and a crotch portion located between the two leg openings. The crotch portion has edges or seams 24 which are located on opposite sides of the crotch portion. The edges or seams 24 extend around each of the leg openings. A portion of the edges or seams 24 normally contact the groin of the wearer when the undergarment 22 is pulled up around the torso 14 and adjusted about the waist 16. The forces acting on the edges or seams 24 of the undergarment 22 in the crotch region 18 cause an upward force which holds the edges or seams 24 in contact with the wearer's body.

Figure 2:
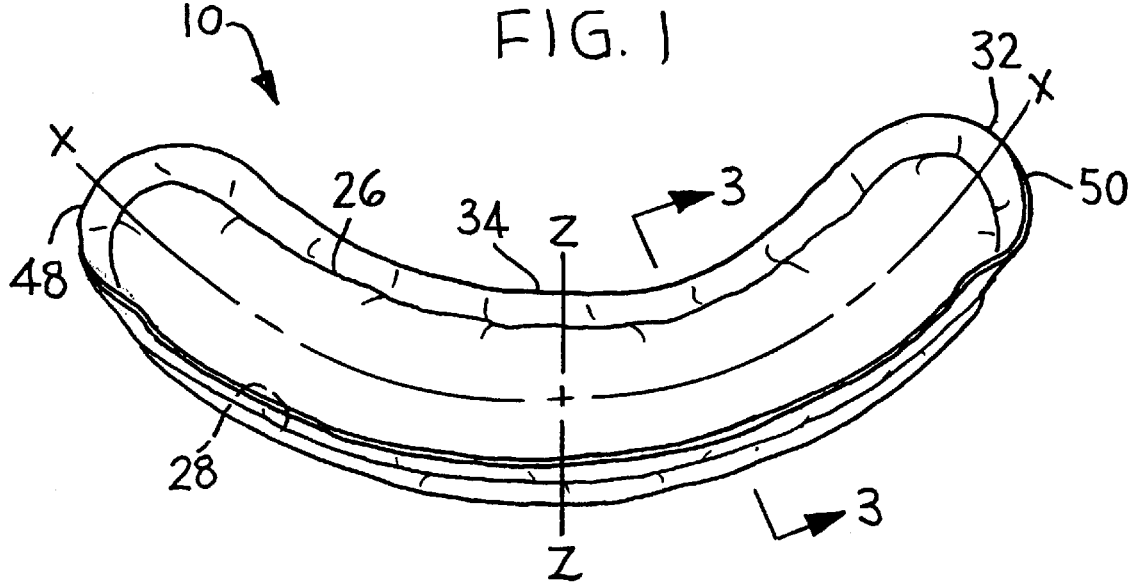
FIG. 2 is a perspective view of a sanitary napkin having first and second channels which are sized and configured to receive the side edges of an undergarment.

Referring to FIG. 2, the sanitary napkin 10 includes a first groove or channel 26 and a second groove or channel 28, both of which are formed in a lower surface thereof. The two edges 24 of the leg openings of the undergarment 22 are designed to enter and/or engage the first and second channels, 26 and 28 respectively. The sanitary napkin 10 also has a first end 30 located adjacent to a front section of the sanitary napkin 10 and an opposite or back end 32 located adjacent to a rear section of the sanitary napkin 10. The first and second ends, 30 and 32 respectively, are located an equal distance from a center point 34 of the sanitary napkin 10. The center point 34 is positioned at the intersection of a longitudinal central axis x—x and a vertical central axis z—z. The grooves or channels 26 and 28 can be offset relative to the center point 34 if desired.

It should be noted that during use, the sanitary napkin 10 can be centered along the vertical central axis $z_1$—$z_1$ of the body, as is shown in FIG. 1, or it can be positioned forward or rearward of the vertical central axis $z_1$—$z_1$, of the body, depending upon the wearers particular preference. It should also be noted that although the sanitary napkin 10 is depicted as being symmetrical in shape with the first and second ends, 30 and 32 respectively, being equally spaced from the center point 34, it is possible to form a non-symmetrical sanitary napkin which varies in shape from one end to the other.

Figure 3:
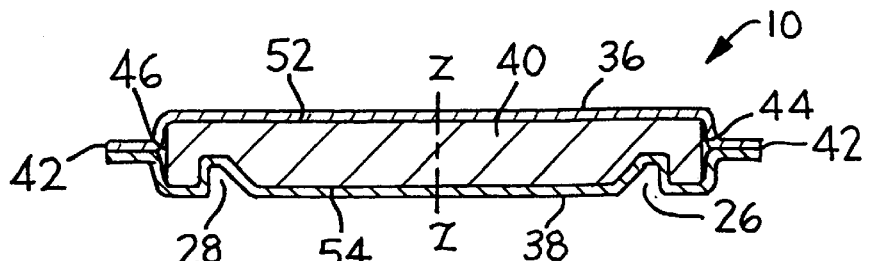
FIG. 3 is a cross-sectional view of the sanitary napkin shown in FIG. 2 taken along line 3—3 which clearly shows the inverted U-shaped configuration of the channels.

Referring now to FIG. 3, the sanitary napkin 10 is shown in more detail. The sanitary napkin 10 includes a liquid permeable cover 36 and a liquid-impermeable baffle 38 which cooperate to enclose an absorbent 40. The cover 36 can be constructed of a natural or synthetic material and should be easily penetrated by body fluids such as menstrual fluid, blood, urine, etc. Suitable materials for the cover 36 include those materials that have a soft hand, such as polyolefin spunbond, which is manufactured and sold by Kimberly-Clark Corporation. The cover 36 could also be made out of a bonded carded web, a polyester, polypropylene, polyethylene, nylon, or other similar type fibers. Other polyolefins, such as linear low density polypropylene, linear low density polyethylene, finely-perforated film webs and net materials can also be used. If a thermoplastic film is used, it will be necessary to aperture, perforate or slit it to make it liquid permeable.

The liquid-impermeable baffle 38 is designed to prevent the passage of liquid out of the sanitary napkin 10. However, the baffle 38 can be constructed to allow or permit the passage of air and moisture vapor out of the sanitary napkin 10 while serving to block the passage of fluids or liquids therefrom. The baffle 38 could also be an air permeable microporous film which will prevent liquids from passing therethrough. The baffle 38 can be a foam, for example, a polyolefin foam or a polyurethane foam. A polyolefin foam can be made from polyethylene or polypropylene. The baffle 38 can also be constructed of a liquid-permeable foam that has been treated or coated to make it liquid-impermeable. Preferably, the baffle 38 is constructed of a very thin thermoplastic film having a thickness of less than about 2 millimeters(mm) and, preferably, less than about 1 mm. Two thermoplastic films which work well are polyethylene and polypropylene. The films can be tinted or made of a special color, such as rose or peach, to make the sanitary napkin 10 more attractive.

Still referring to FIG. 3, one will notice that the cover 36 and the baffle 38 are bonded or sealed together to form a peripheral seal 42. This peripheral seal 42 extends completely around the absorbent 40 and encloses the absorbent 40. If one desires, one can form what is known as a wrapped pad wherein the baffle 38 is positioned adjacent to a lower surface of the absorbent 40 and the cover 36 is completely wrapped about both the absorbent 40 and the baffle 38. The cover 36 will then be bonded or secured to itself along a lower surface of the sanitary napkin 10. Various other ways of assembling the cover, absorbent and baffle are known to those skilled in the art and various alternatives could be employed for this invention.

The absorbent 40 is positioned between the cover 36 and the baffle 38. The absorbent 40 has a first longitudinally-extending side 44 and a second longitudinally-extending side 46. The absorbent 40 also has a first end 48 and a second end 50 which are shown as a dotted lines in FIG. 2. The absorbent 40 also has a body facing surface 52 and a garment facing surface 54. The body facing surface 52 faces toward the body of the wearer of the sanitary napkin 10 but is not necessarily in contact with the body, although it may be. The body facing surface 52 of the absorbent 40 is normally covered by the cover 36. The garment facing surface 54 of the absorbent 40 faces the undergarment 22 but is not necessarily in contact with the undergarment 22. The garment facing surface 54 is normally covered by the baffle 36 although it does not have to be.

For purposes of discussion, the absorbent 40 will be described as a single absorbent layer. However, it should be noted that the absorbent 40 can be made up of one or more absorbent layers or be a combination of one or more layers interspersed with a superabsorbent material. The absorbent 40 can be made from natural or synthetic fibers or a blend thereof. Natural fibers include cellulose fibers such as wood pulp, cotton or regenerated cellulose. Synthetic fibers can include polyesters or polyolefins with polyethylene or polypropylene fibers being preferred. The absorbent 40 can also be constructed from coform, which is a blend of wood pulp and synthetic meltblown fibers. When synthetic fibers are used, the fibers can be treated with a surfactant so as to increase their wettability.

The absorbent 40 can also contain a hydrocolloidal material, commonly referred to as a superabsorbent. Superabsorbents are normally added to the absorbent to increase the amount of fluid which the absorbent can contain and also to increase fluid retention capabilities. The superabsorbent can be added as individual particles or it can be formed as a laminate structure having a superabsorbent material incorporated onto a carrier sheet.

Still referring to FIG. 3, one will notice that the first and second grooves or channels, 26 and 28 respectively, are formed in a lower surface of the absorbent 40 and the baffle 38 follows the contours of the first and second channels, 26 and 28 respectively. This arrangement permits the first and second channels, 26 and 28 respectively, to be visible in the finished product. It is also possible to form the first and second channels, 26 and 28 respectively, in the lower surface of the sanitary napkin 10 and then stretch or bridge the baffle 38 across the channels 26 and 28. When this is done, the baffle 38 will not follow the contour of the channels 26 and 28. The engagement of the edges or seams 24 of the undergarment 22 will cause the baffle 38 to stretch and be forced up into the first and second channels, 26 and 28 respectively. Preferably, the baffle 38 will be formed such that it enters the first and second channels, 26 and 28 respectively, and the first and second channels, 26 and 28 respectively, will be visible to the ultimate consumer when the sanitary napkin 10 is ready to by used. For sanitary napkins in particular, it is common to individually wrap each napkin in its own wrapper to keep it clean and sanitary. The wrapper can be made out of a thermoplastic material such as polyethylene or polypropylene.

Referring now to FIGS. 4–8, several embodiments are shown depicting different arrangements, sizes and configurations for the first and second channels, 26 and 28 respectively. For simplicity reasons only, only the absorbent layer 40 is shown with the first and second grooves or channels, 26 and 28 respectively, formed in the garment facing surface 54. For purposes of discussion, like numerals will be used for the longitudinally-extending sides, 44 and 46 respectively, and the body facing and garment facing surfaces, 52 and 54 respectively, of the absorbent 40 throughout FIGS. 4–8. The only difference will be the numbers used to designate the channels.

Figure 4:
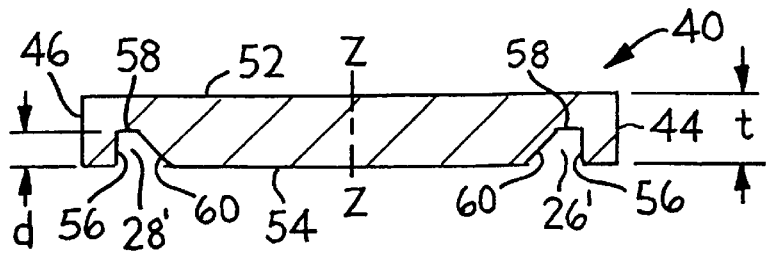
FIG. 4 is a cross-sectional view of an absorbent layer having a pair of channels with each channel having a notched configuration including a tapered interior wall.

In FIG. 4, the absorbent 40 contains a first groove or channel 26' and a second groove or channel 28'. Each of the first and second channels, 26' and 28' respectively, contain a vertical side wall 56, a horizontal base 58 and a tapered side wall 60. Each of the tapered side walls 60 extends from the horizontal base 58 to the garment facing surface 54. The tapered side walls 60 are aligned closest to the longitudinal central axis x—x while the vertical side walls 56 are located outward therefrom and adjacent to the respective first and second longitudinal sides, 44 and 46. The two channels 26' and 28' are spaced apart from one another and each is located on an opposite side of the longitudinal central axis x—x. The first and second channels, 26' and 28' respectively, can be linear or non-linear. Preferably, the first and second channels, 26' and 28' respectively, are aligned parallel to one another or are a mirror image of one another if non-linear with respect to the longitudinal central axis x—x. The depth (d) of the first and second channels, 26' and 28' respectively, can vary but preferably is at least about 0.1 inches (about 2.5 mm), and most preferably, is from about 0.1 inch to about 0.5 inches (about 2.5 mm to about 13 mm). Since the thickness (t) of the absorbent 40 can vary along the longitudinal central axis x—x, another way of stating the depth (d) of each of the first and second channels, 26' and 28' respectively, is that the depth (d) of the channel 26' and 28' can range from between about 10 percent to about 90 percent of the thickness (t) of the absorbent layer 40. Preferably, the depth (d) will range from between about 10 percent to about 75 percent of the thickness (t) of the absorbent 40. More preferably, the depth (d) of the channels 26' and 28' will range from between about 20 percent to about 50 percent of the thickness (t) of the absorbent 40. Most preferably, the depth (d) of the channels 26' and 28' will range from between about 25 percent to about 50 percent of the thickness (t) of the absorbent 40.

It should be noted that when the absorbent 40 is comprised of more than one layer, the depth (d) of the first and second channels, 26' and 28' respectively, will be a percentage of the thickness (t) of the absorbent 40 at a particular location. It should also be noted that when the absorbent 40 is formed with a hump along the longitudinal central axis x—x line or is contoured in some fashion, that the portion of the absorbent 40 having the first and second channels, 26' and 28' respectively, may be of a reduced thickness (t) than the maximum thickness of the absorbent 40.

Figure 5:
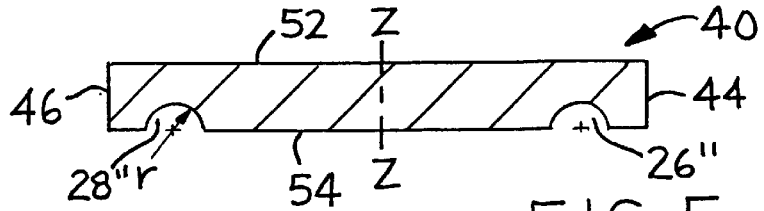
FIG. 5 is a cross-sectional view of an absorbent layer having a pair of channels with each channel having a semi-circular configuration.

Referring now to FIG. 5, an alternative configuration of the first and second channels is shown. The absorbent layer 40 contains a first groove or channel 26" and a second groove or channel 28". The first and second channels, 26" and 28" respectively, are in the form of an inverted semicircle which has a radius "r" of at least about 0.01 inches (about 0.25 mm), and preferably, a radius "r" of from between about 0.01 inches to about 0.25 inches (about 0.25 mm to about 6.4 mm). The first and second channels, 26" and 28" respectively, can be linear or non-linear. The first and second channels, 26" and 28" can extend along a portion of the length of the absorbent 40 or they can extend along the entire length of the absorbent 40.

Figure 6:
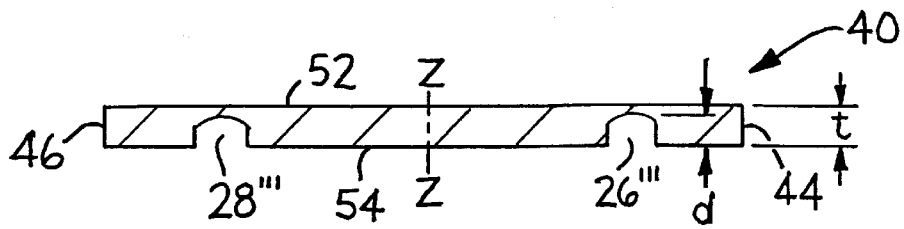
FIG. 6 is a cross-sectional view of a thin absorbent layer having a pair of channels with each channel having a semi-circular configuration and each channel having a depth which extends further into the absorbent layer.

Referring to FIG. 6, still another configuration of the first and second channels is depicted. The thin absorbent 40 has first and second grooves or channels, 26''' and 28''' respectively, formed therein. The first and second channels, 26''' and 28''' respectively, are in the form of an inverted U which extend into the absorbent 40 to a greater extent than that shown in FIG. 5. For example, the depth (d) of the first and second channels, 26''' and 28''' respectively, can be from between about 50 percent to about 95 percent of the thickness (t) of the absorbent 40. Preferably, the depth (d) of the first and second channels, 26''' and 28''' respectively, can be from between about 70 percent to about 95 percent of the thickness (t) of the absorbent 40, and most preferably, the depth (d) of the first and second channels, 26''' and 28''' respectively, can be from between about 75 percent to about 90 percent of the thickness (t) of the absorbent 40. The first and second channels, 26''' and 28''' respectively, can be linear or non-linear. The first and second channels, 26''' and 28''' respectively, can extend along a portion of the length of the absorbent 40 or they can extend along the entire length of the absorbent 40. The length of the first and second channels, 26''' and 28''' respectively, can extend a distance of from between about 25 percent to 100 percent of the length of the absorbent 40. Preferably, the length of the first and second channels, 26''' and 28''' respectively, can extend a distance of from between about 25 percent to about 75 percent of the length of the absorbent 40, and most preferably, from about 30 percent to about 70 percent of the length of the absorbent 40. One should note that when a sanitary napkin 10 has a peripheral seal 42, the overall or total length of the sanitary napkin 10 will be larger than the overall length of the absorbent 40.

Figure 7:
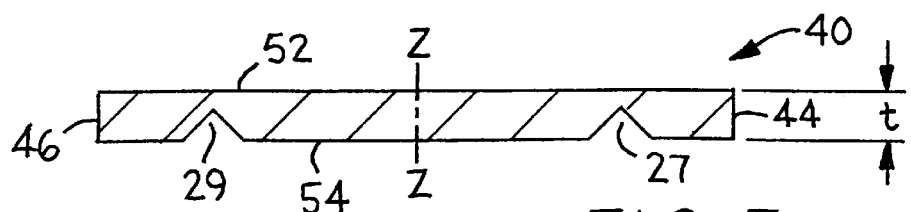
FIG. 7 is a cross-sectional view of a thin absorbent layer having a pair of channels with each channel having an inverted V-shaped configuration and with each channel spaced a greater distance outward from the longitudinal centerline.

Referring to FIG. 7, a thin absorbent 40 is shown having a much greater overall width. Formed in the garment-facing surface 54 of the absorbent 40 are a first groove or channel 27 and a second groove or channel 29, both of which have an inverted V-shaped configuration. The depth of the V-shaped configuration can extend inward into the absorbent from between about 10 percent to about 90 percent of the total thickness (t) of the absorbent 40. Preferably, the V-shaped notch will extend inward into the absorbent 40 an amount of between about 20 percent to about 75 percent of the total thickness (t) of the absorbent 40, and most preferably, from between about 25 percent to about 50 percent of the thickness (t) of the absorbent 40. The first and second channels, 27 and 29 respectively, correspond to the channels 26 and 28, 26' and 28', and 26" and 28" in their function. When the first and second channels, 27 and 29 respectively, are linear, they can be spaced inward at least about 0.25 inches (about 6.4 mm) from the first and second longitudinally-extending sides, 44 and 46 respectively. Preferably, the first and second channels, 27 and 29 respectively, are spaced inward at least about 0.5 inches (about 13 mm) from the first and second longitudinally-extending sides, 44 and 46 respectively. When the channels 26 and 28 are non-linear, the ends of each channel can extend to the first and second longitudinally-extending sides, 44 and 46 respectively.

Figure 8:
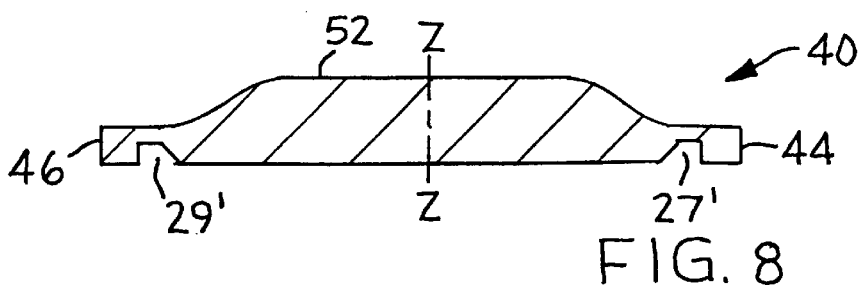
FIG. 8 is a cross-sectional view of a contoured absorbent layer having a notched channel configuration with a tapered interior wall.

Referring to FIG. 8, an embodiment of an absorbent 40 is shown wherein the absorbent has a contoured surface which is thicker along the longitudinal central axis x—x and thinner adjacent to the first and second longitudinally-extending sides, 44 and 46 respectively. In this embodiment, the first and second channels, 27' and 29' respectively, have a similar configuration as the first and second channels, 26' and 28' respectively, shown in FIG. 4. However, the first and second channels, 27' and 29' respectively, are located in the thinner outer regions of the absorbent 40. One will notice that in FIG. 8, the first and second channels, 27' and 29' respectively, are located a greater distance from the longitudinal central axis x—x than are the first and second channels, 26' and 28' respectively, which are shown in FIG. 4. It is envisioned that the width of the sanitary napkin 10 and the location of the first and second channels, 27' and 29' respectively, will be sized such that the crotch region 18 of the undergarment 22 will not have to be substantially altered when the side edges 24 of the undergarment 22 contact the sanitary napkin 10. In addition, the first and second channels, 27' and 29' respectively, should be so located that they will force the absorbent 40 into contact with the groins of the user.

One will notice when comparing FIGS. 7 and 8, that the channels 27 and 29 are located a greater distance away from the longitudinal central axis x—x in FIG. 7 than in FIG. 6. This size difference may be advantageous in accommodating different crotch regions of women where the distance between the groin varies depending upon one's anatomy. It may also be advantageous for a consumer who wears a certain type of undergarment to wear an absorbent article such that the side edges 24 of the undergarment 22 will comfortably fit into the first and second channels, 27 and 29 respectively.

It should be also noted that the first and second channels 26 and 28, 26' and 28', 26" and 28", 26'" and 28'", 27 and 29 as well as 27' and 29' can be formed in the garment facing surface 54 of the absorbent 40 in a number of different ways. The channels can be cut into the absorbent using a knife or rotary cutter, or they can be embossed into the absorbent. The channels can also be made by forming two spaced apart, raised humps in a mold such that the channels will be present after the absorbent material fills the mold. The channels can also be formed by other means known to those skilled in the art. Forming the channels by embossing may be the easiest to implement. The molding process is advantageous in that both of the channels can be simultaneously formed.

Figure 9:
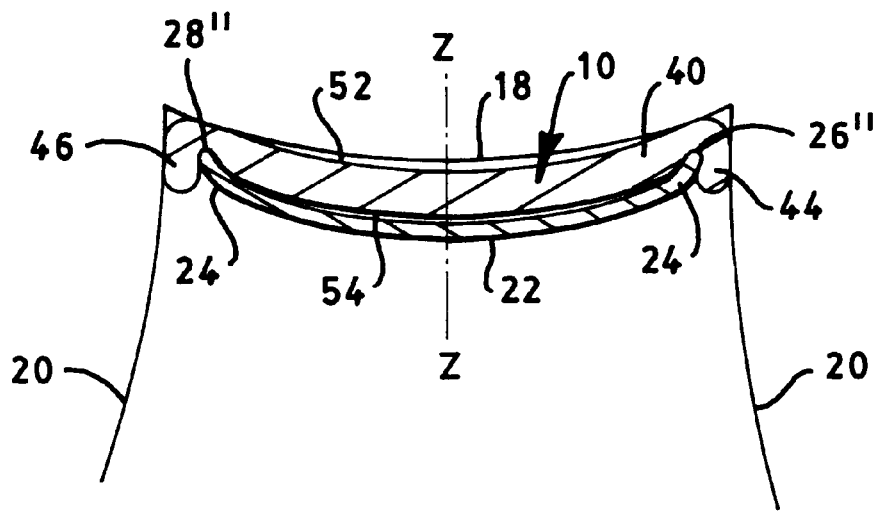
FIG. 9 is a schematic view of the crotch region of a human body with a sanitary napkin held against the pudendum by the side edges of an undergarment engaged in the channels formed in the sanitary napkin.

Referring to FIG. 9, the sanitary napkin 10 is shown positioned adjacent to the crotch region 18 of the wearer. The sanitary napkin 10 is retained in position by the undergarment 22. The side edges 24 of the undergarment 22 contact and enter into the channels 26" and 28" so as to force the sanitary napkin 10 up against and secure to the body of the wearer. The sanitary napkin 10 will move upward until the first and second longitudinally-extending sides, 44 and 46 respectively, contact the groins of the wearer. In FIG. 9, one will notice that the thighs of the legs 20 are depicted so as to show the normal position of the sanitary napkin 10 when placed adjacent to the body. During normal movement of the torso 14 and the legs 20, such as walking, standing, sitting, running, etc. the thighs may move closer together and the sanitary napkin 10 may be squeezed. However, the forces working on the leg openings of the undergarment 22 will cause the side edges 24 to keep the sanitary napkin 10 secure against the body.

Figure 10:
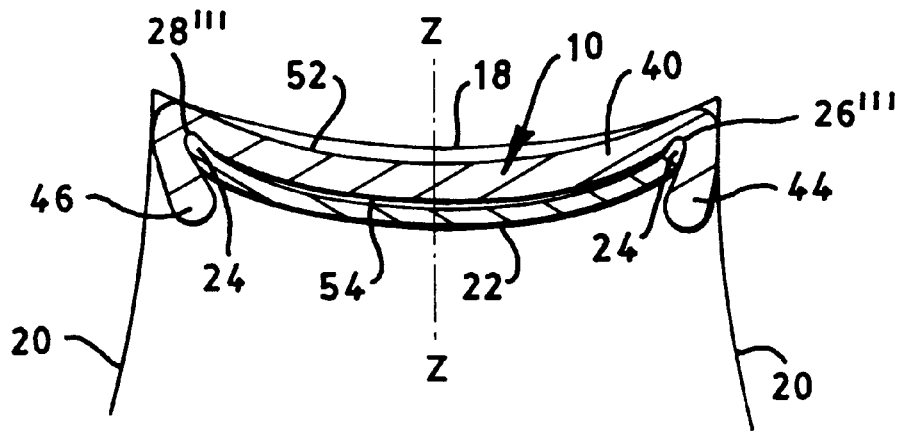
FIG. 10 is a schematic view of the crotch region of a human body with a wider sanitary napkin held against the pudendum by the side edges of an undergarment engaged in the channels formed in the sanitary napkin.

Referring to FIG. 10, the sanitary napkin 10 is shown having an absorbent 40 with a greater width, as is depicted in FIG. 6. Since the absorbent 40 is wider than the absorbent depicted in FIG. 9, one will notice that the first and second longitudinally-extending sides, 44 and 46 respectively, of the absorbent 40 will extend downward from the groin area and provide added protection against fluid leakage. The function of the undergarment 22 relative to the sanitary napkin 10 is the same as denoted above in relation to FIG. 9. It should be noted that in FIGS. 9 and 10, the cover 36 and the baffle 38 have been removed for simplicity purposes only. If the sanitary napkin 10 contains both a cover 36 and a baffle 38, both of them would be present in actual use.

Turning now to FIGS. 11–22, a number of alternative arrangements for the channels 26 and 28 are depicted. For purposes of understanding, all the articles will be referred to as sanitary napkins 10 having an absorbent 40 and having first and second grooves or channels, 26 and 28 respectively. When more than two channels are present, additional numbers will be given to the additional channels.

Figure 12:
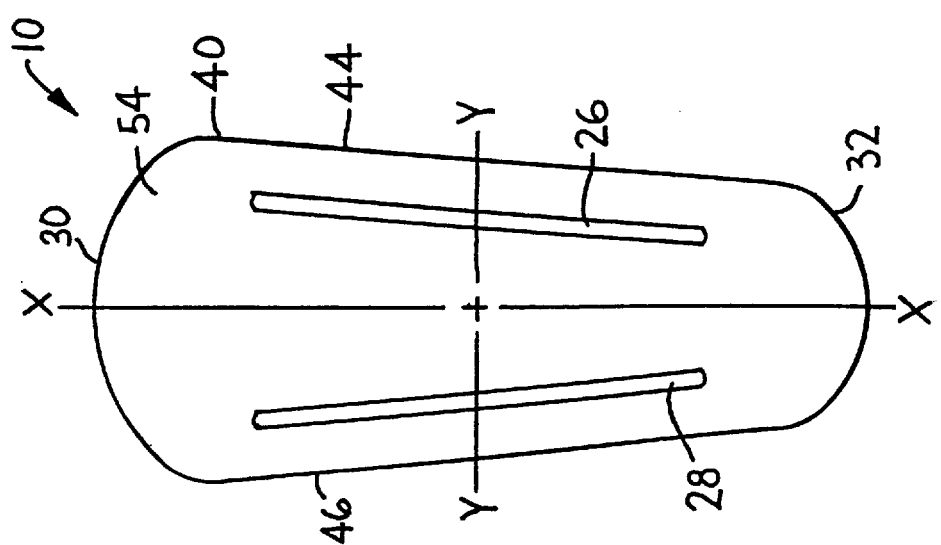
FIG. 12 is a bottom view of an absorbent article having tapered longitudinal sides and a pair of longitudinally extending grooves or channels formed therein formed parallel to the longitudinal sides.

In FIG. 12, a bottom view of a sanitary napkin 10 is shown having a pair of longitudinally-extending channels, 26 and 28 which are arranged parallel to the first and second longitudinally-extending sides, 44 and 46 respectively. The first and second channels, 26 and 28 respectively, are linear and do not extend the entire length of the absorbent 40. Instead, the first and second channels, 26 and 28 respectively, extend a substantial length of from between about 50 percent to about 90 percent of the total length of the absorbent 40. Preferably, the first and second channels, 26 and 28 respectively, extend from between about 60 percent to about 80 percent of the total length of the absorbent 40, and most preferably, from between about 70 percent to 75 percent of the total length of the absorbent 40. The reason that the first and second channels, 26 and 28 respectively, do not have to extend the entire length of the absorbent 40 is that the bottom surface of the sanitary napkin 10 will be convex relative to the body, and therefore, the central portion of the sanitary napkin 10 is really the critical area in which the side edges 24 of the undergarment 22 must enter into the first and second channels, 26 and 28 respectively.

The sanitary napkin 10 is shown having a longitudinal central axis x—x and a transverse central axis y—y. The first and second channels, 26 and 28 respectively, can be formed into the garment-facing 54 of the absorbent 40 such that they extend longitudinally outward an equal amount from the transverse central axis y—y. In addition, they can be equally spaced apart from the longitudinal central axis x—x. Furthermore, each of the first and second channels, 26 and 28 respectively, are spaced inwards at least about 0.25 inches (about 6.4 mm), and preferably, at least about 0.5 inches (about 13 mm) from the respective first and second longitudinally-extending sides, 44 and 46 respectively. The first and second channels, 26 and 28 respectively, can also be arranged parallel to one another. The first and second channels, 26 and 28 respectively, will have a width of between about 0.1 inches (about 2.5 mm) to about 0.5 inches (about 13 mm), a depth of between about 0.1 inches (about 2.5 mm) to about 0.5 inches (about 13 mm), and a length of at least about 3 inches (about 7.6 mm). Preferably, the length of the first and second channels, 26 and 28 respectively, is from between about 3 inches (about 7.6 mm) to a distance equal to the length of the sanitary napkin 10. Most preferably, the length of the first and second channels, 26 and 28 respectively, is from between about 3.5 inches (about 8.9 mm) to about 4.5 inches (about 11.4 mm).

Referring to FIG. 12, an embodiment is shown of a sanitary napkin 10 having longitudinally-extending sides 44 and 46 that are tapered. Such longitudinally-extending sides give the sanitary napkin 10 a non-symmetrical shape such that the front end 30 is wider than the opposite or back end 32. The first and second channels, 26 and 28 respectively, are formed in the lower surface 54 of the absorbent 40 and are arranged at an angle to one another so as to be parallel with the longitudinally-extending sides, 44 and 46 respectively. As with FIG. 11, the first and second channels, 26 and 28 respectively, do not extend the entire length of the absorbent 40 but only extend along a substantial portion thereof. By substantial portion it is meant an amount greater than about 50 percent of the total length of the absorbent 40.

Figure 13:
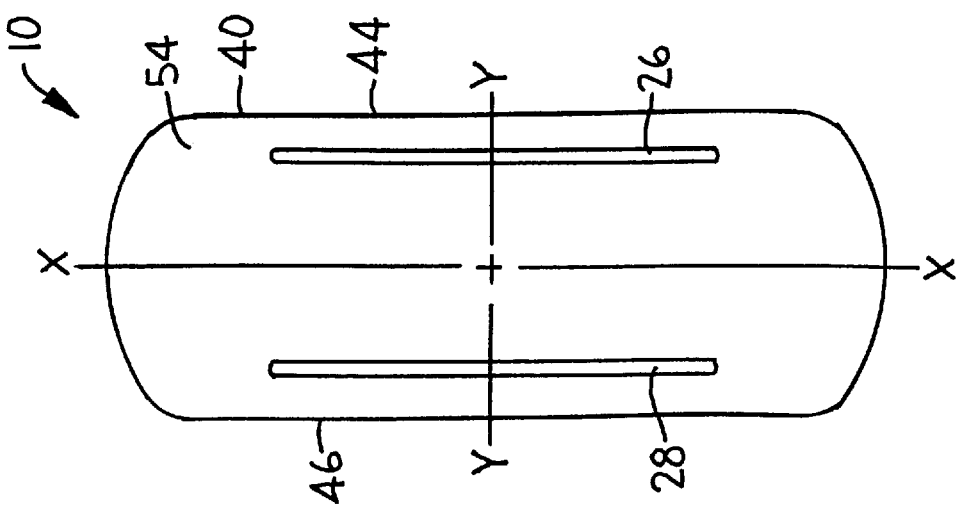
FIG. 13 is a bottom view of an absorbent article having an hourglass configuration and a pair of arcuately extending grooves or channels formed therein.

Referring to FIG. 13, a sanitary napkin 10 having an hourglass shape is shown. The sanitary napkin 10 has first and second grooves or channels, 26 and 28 respectively, which are non-linear, and preferably, arcuate in shape. The first and second longitudinally-extending sides, 44 and 46 respectively, are non-linear and each of the first and second channels, 26 and 28 respectively, are aligned parallel to one of these longitudinally-extending sides, 44 and 46 respectively. The first and second channels 26 and 28 respectively, can also be arranged so as to be a mirror image of one another with respect to the longitudinal central axis x—x. The hourglass shaped sanitary napkin 10 is preferred for there is less absorbent material in the center of the crotch region along the transverse central axis y—y and this creates a more comfortable sanitary napkin when worn. The first and second channels, 26 and 28 respectively, do not extend the entire length of the absorbent article 10. As denoted above for FIGS. 11 and 12, the first and second channels 26 and 28 respectively, can extend along a substantial length of the sanitary napkin 10. By "substantial length" is meant an amount greater than about 50 percent of the length of the absorbent 40.

Figure 11:
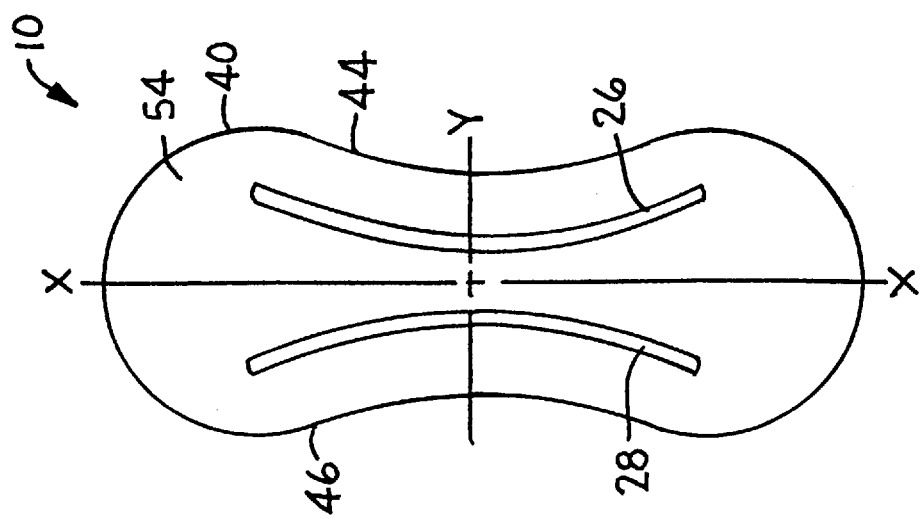
FIG. 11 is a bottom view of an absorbent article having at pair of longitudinally extending grooves or channels formed therein.
Figure 16:
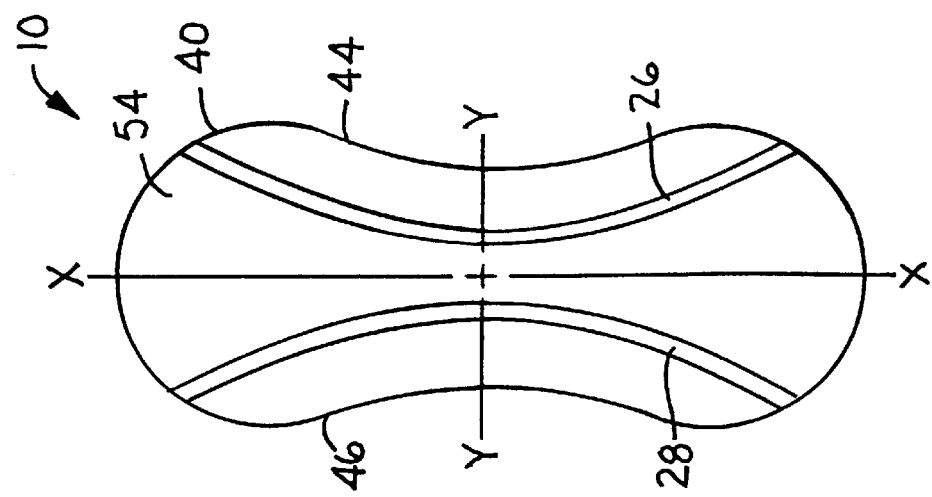
FIG. 16 is a bottom view of an absorbent article having an hourglass configuration with a pair of grooves or channels formed therein which extend a substantial distance along the entire length of the absorbent article.
Figure 15:
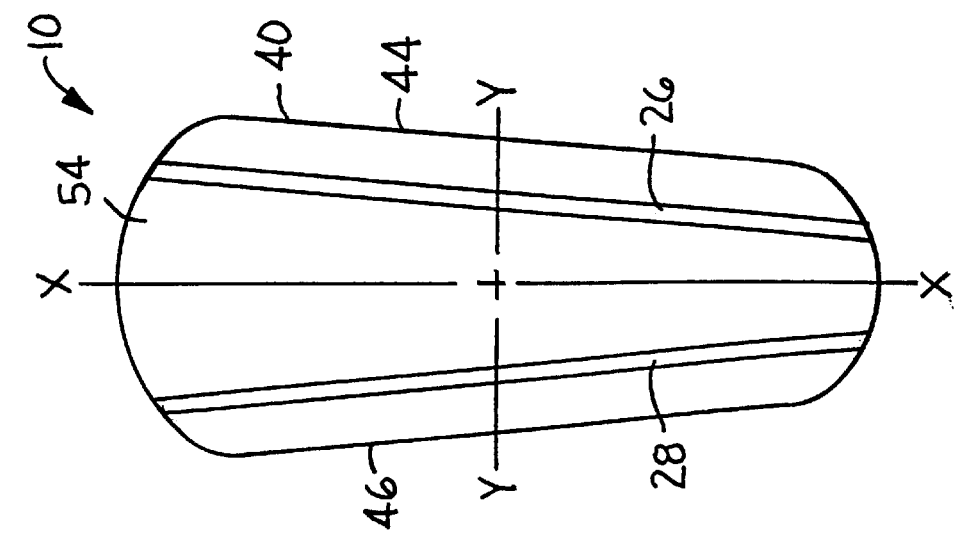
FIG. 15 is a bottom view of an absorbent article having tapered longitudinally-extending sides and having a pair of linear grooves or channels formed therein which extend the entire length of the absorbent article.
Figure 14:
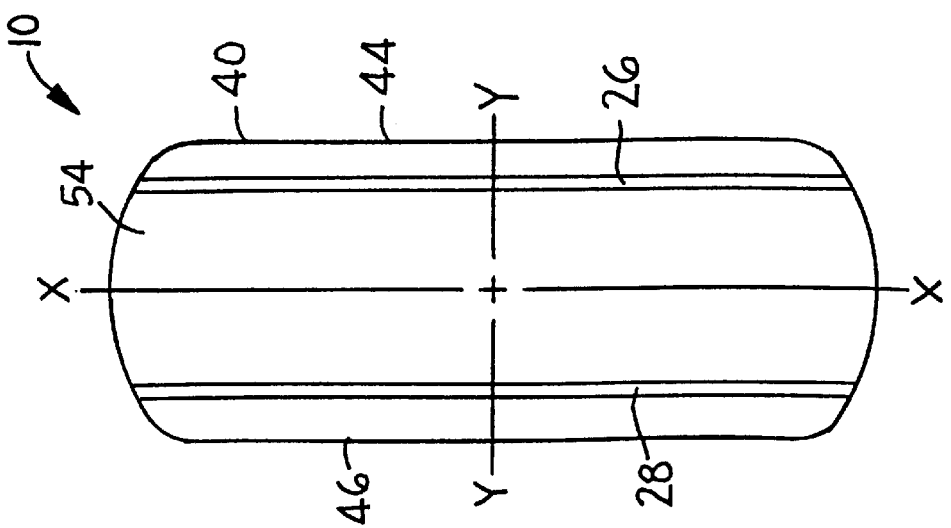
FIG. 14 is a bottom view of an absorbent article having a pair of linear grooves or channels formed therein which extend the entire length of the absorbent article.

Referring to FIGS. 14–16, one will notice that the sanitary napkins tend to coincide with those depicted in FIGS. 11, 12 and 13 respectively. The only difference being that the first and second grooves or channels, 26 and 28 respectively, extend essentially the entire length of the absorbent 40. Depending upon the particular configuration of each of the sanitary napkins, by "essentially the entire distance" is meant a distance of between about 90 percent to 100 percent of the length of the absorbent 40. The reason why the first and second channels, 26 and 28 respectively, may not extend the entire length of the absorbent article 10 is that the ends of the sanitary napkin 10 may be rounded and the first and second channels, 26 and 28 respectively, may be arcuate in shape. Therefore, it would be difficult to form the first and second channels, 26 and 28 respectively, such that they extend to the tip of the rounded portion of the absorbent 40.

In FIGS. 14 and 15, one will notice that the first and second channels, 26 and 28 respectively, are linear and are arranged parallel to the longitudinally-extending sides, 44 and 46 respectively. While in FIG. 16, the first and second channels 26 and 28 respectively, are non-linear and are aligned parallel to the longitudinally-extending sides, 44 and 46 respectively.

Figure 19:
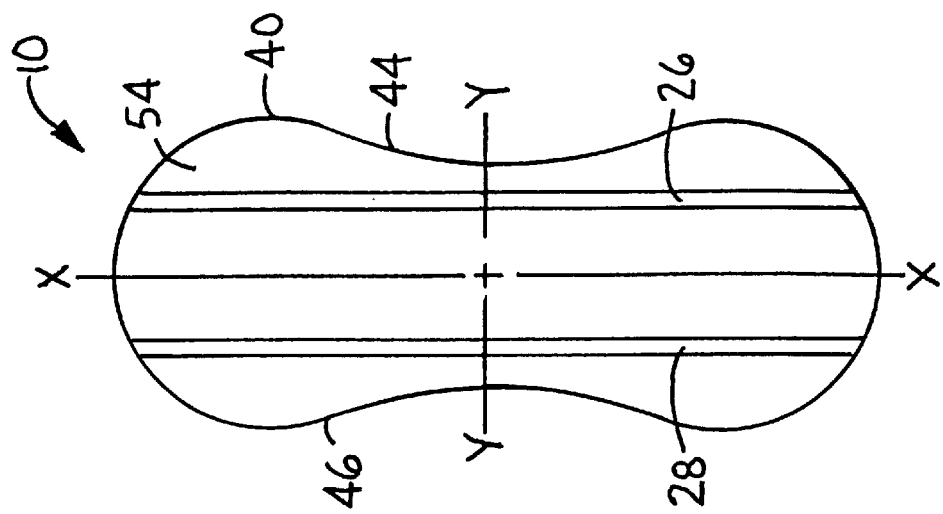
FIG. 19 is a bottom view of an absorbent article having an hourglass configuration with a pair of linear grooves or channels formed therein which extend substantially the entire distance along the length of the absorbent article.
Figure 18:
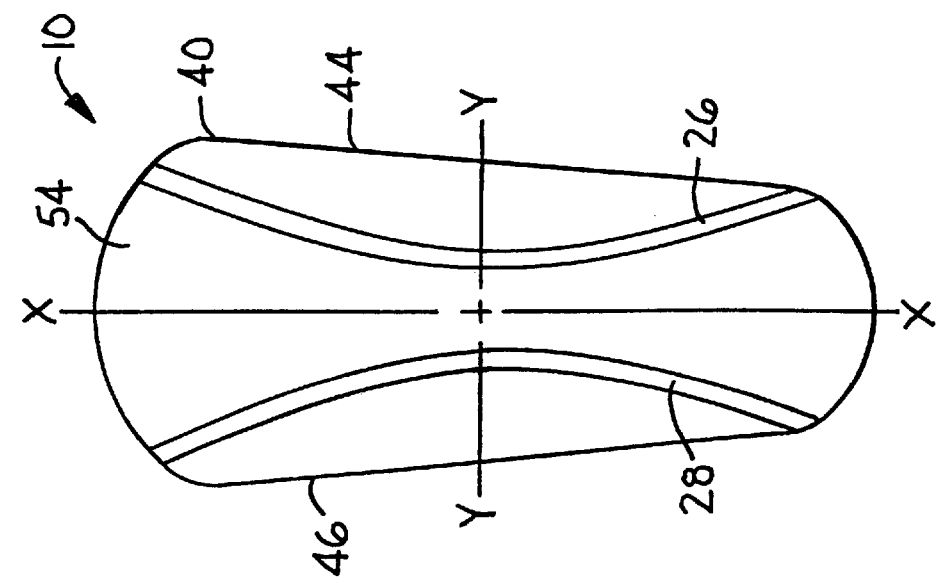
FIG. 18 is a bottom view of an absorbent article having tapered longitudinal sides and having a pair of non-linear grooves or channels formed therein which extend essentially the entire length of the absorbent article.
Figure 17:
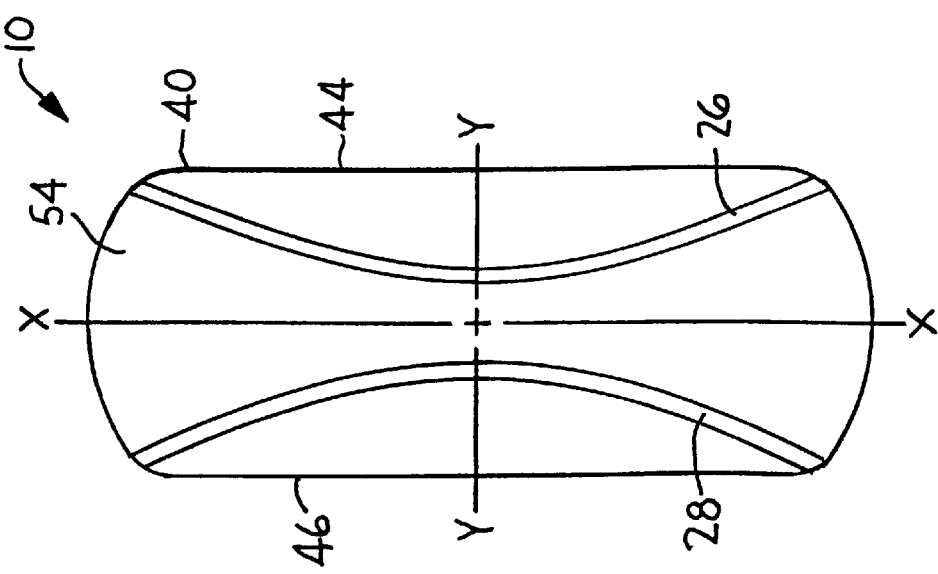
FIG. 17 is a bottom view of an absorbent article having a pair of non-linear grooves or channels formed therein which extend essentially the entire length of the absorbent article.

Turning now to FIGS. 17–19, one will notice that the sanitary napkins 10 are similar to those depicted in FIGS. 14–16 except that the first and second grooves or channels, 26 and 28 respectively, are different in configuration. In FIG. 17, the first and second channels, 26 and 28 respectively, are non-linear in configuration. Preferably, the first and second channels, 26 and 28 respectively, have an arcuate profile and therefore cannot be aligned parallel with the longitudinally-extending sides, 44 and 46 respectively. In FIG. 18, the first and second channels, 26 and 28 respectively, are again arcuate in design and are not parallel to the longitudinally-extending sides, 44 and 46, which are illustrated as being tapered. In FIG. 19, the first and second channels, 26 and 28 respectively, are linear and therefore cannot be parallel to the longitudinally-extending sides, 44 and 46, which are illustrated as being hourglass shaped. One will notice that in FIGS. 17–19, the first and second channels, 26 and 28 respectively, extend essentially the entire length of the absorbent 40.

Referring to FIGS. 20–22, three embodiments are shown wherein each sanitary napkin 10 contains multiple channels formed in the garment facing surface 54 of the absorbent 40. In FIG. 20, two pair of channels 62 and 64, and 66 and 68, are formed having an arcuate profile and are arranged such that the channels 62 and 64 are much smaller and located farther away from the longitudinal central axis, x—x than are the channels 66 and 68 respectively. Channels 66 and 68, have a longer overall length than the first and second channels, 62 and 64 respectively. The two pairs of channels 62 and 64, and 66 and 68, can be symmetrically arranged about the longitudinal central axis x—x or the transverse central axis y—y if one so desires.

Referring to FIG. 21, one will notice a sanitary napkin 10 with two pair of channels formed in the garment facing surface 54 of the absorbent 40. The first pair of channels 62 and 64 are linear in configuration and extend essentially the entire length of the absorbent 40. The first pair of channels 62 and 64 are located at a greater distance from the longitudinal central axis x—x than are the second pair of channels 66 and 68. The second pair of channels 66 and 68 are also linear and extend along the entire length of the absorbent 40. Because of the rounded ends of the sanitary napkin 10, the overall length of the second pair of channels 66 and 68 is slightly greater than the length of the first pair of channels 62 and 64. All of the channels can be arranged parallel to one another as well as parallel to the longitudinally-extending sides, 44 and 46 respectively, if desired. The benefit of providing multiple channels in the garment-facing surface 54 of the absorbent 40 is that the sanitary napkin 10 can be used with undergarments 22 having various width crotch regions 18. Some undergarments 22 have a narrower crotch region 18. By forming two or more pair of channels in the absorbent 40, one can use the sanitary napkin 10 with a variety of undergarments 22 having crotch regions 18 of different widths. Likewise, some consumers may find it more advantageous to have the edges 24 of the undergarment 22 positioned in alignment with their groins while others may prefer the edges 24 of the undergarment 22 to be located closer to the longitudinal central axis center x—x of the sanitary napkin 10.

Referring to FIG. 22, a sanitary napkin 10 is shown having three pair of channels 62 and 64, 66 and 68, and 70 and 72 formed in the lower or garment facing surface 54 of the absorbent 40. The three pair of channels are all arcuate in shape and vary in length relative to their position on the absorbent article 10. The first pair of arcuate shaped channels 62 and 64 have the shortest length and are located at the outer most edge of the sanitary napkin 10. The second pair of channels 66 and 68 are located inward of the first pair of channels 62 and 64 and have a slightly longer length. The third pair of channels 70 and 72 have the longest length and are located inboard of the first and second pair of channels, 62 and 64, and 66 and 68 respectively. As stated earlier, the formation of multiple channels in the lower surface of the absorbent 40 provides versatility to the ultimate consumer. It also allows the ultimate consumer to use the sanitary napkin 10 with a variety of undergarments having a crotch region of different width.

Figure 23:
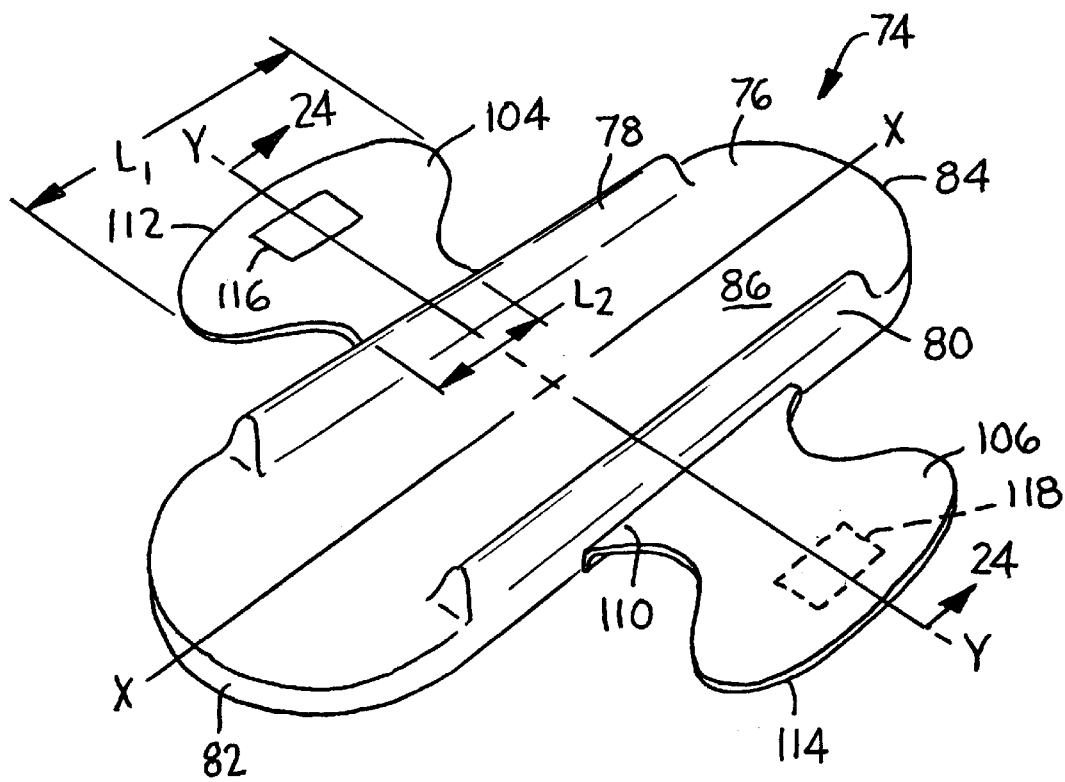
FIG. 23 is a schematic view of an absorbent article having a pair of raised longitudinally-extending sides and a pair of flaps depending downwardly and inwardly from the raised sides.
Figure 24:
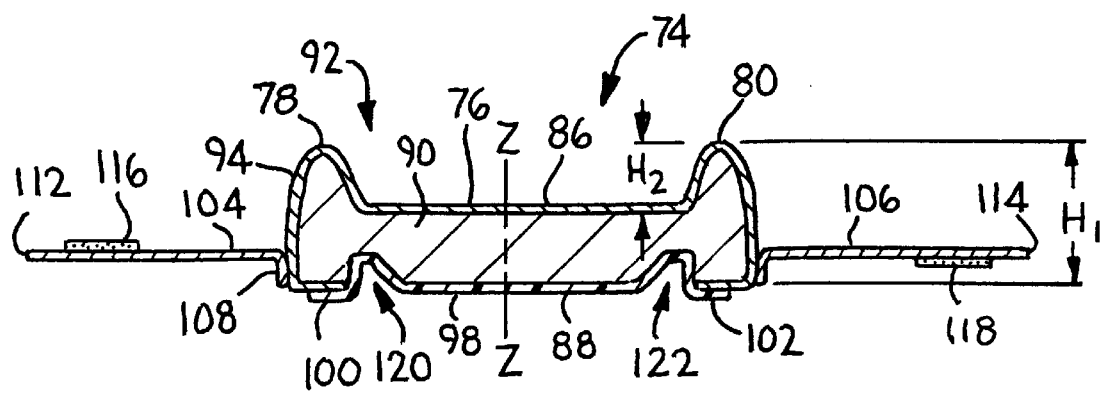
FIG. 24 is a cross-sectional view of the absorbent article shown in FIG. 23 taken along line 24—24.

Referring to FIGS. 23 and 24, an absorbent article 74 is shown having a body contacting surface 76 with a first raised longitudinally extending side 78 and a second raised longitudinally extending side 80. The absorbent article also has a first end 82 and a second end 84. As best seen in FIG. 24, the absorbent article 74 includes a liquid permeable cover 86 and a liquid-impermeable baffle 88 which cooperate to enclose an absorbent 90. The cover 86, the baffle 88 and the absorbent 90 are formed into an absorbent pad 92. The first and second raised longitudinally-extending sides, 78 and 80 respectively, are formed on the upper or body contacting surface 76. Each of the raised longitudinally-extending sides, 78 and 80 respectively, has a vertically oriented outer surface, 94 and 96 respectively. By "vertically oriented" means that the outer surfaces 94 and 96 can be aligned parallel to the central vertical axis z—z or be aligned at an acute angle thereto. It should be noted that the vertical outer surfaces 94 and 96 can be linear or non-linear. When non-linear, they can be curved or arcuate in configuration. The pad 92 also has a garment facing surface 98 aligned opposite to the body facing surface 76. The garment facing surface 98 is designed to face the inner crotch portion of an undergarment.

In FIG. 24, one will notice that the cover 86 and the baffle 88 are joined together at locations 100 and 102, respectively, which are located on the garment facing surface 98. However, the point adjoining can be along the vertical outer surfaces 94 and 96 if desired. Alternatively, the baffle 88 and the absorbent 90 can be completely enclosed by the cover 86 if desired.

The absorbent article 74 also contains a pair of flaps 104 and 106 which have sufficient size to extend around at least a portion of the crotch of an undergarment. Preferably, the flaps 104 and 106 will overlap and be attached to one another. Alternatively, the flaps 104 and 106 can be attached or secured to the outer surface of the crotch portion of an undergarment. Each of the flaps, 104 and 106 respectively, has a proximal edge, 108 and 110 respectively, and a distal edge, 112 and 114 respectively. Each of the proximal edges 108 and 110 are affixed to one of the vertically oriented outer surfaces, 94 and 96 respectively. Each of the distal edges 112 and 114 extend downward and inward around the crotch portion of an undergarment. It is important to note that the flaps 104 and 106 are not designed to extend upward into the groins of the user since the raised longitudinally-extending sides, 78 and 80 respectively, will serve that function. Instead the pair of flaps 104 and 106 depend downwardly and inwardly around the crotch portion of an adjacent undergarment so as to prevent staining of the undergarment by any body fluid that may leak off of the absorbent article 74.

The pair of flaps 104 and 106 can be made into any desired size and shape provided that they have a width along the transverse central axis y—y sufficient to overlap when they wrap around the undergarment. However, for best results the flaps 106 and 104 should be centrally located on the absorbent article 74 such that they bifurcate the central transverse axis y—y. It is also advantageous to form the flaps 104 and 106 such that they have a length $L_1$ measured along the distal edges, 112 and 114 respectively, which is longer than a length $L_2$ measured at the proximal edges 108 and 110 respectively. The length $L_1$ of each of the flaps 104 and 106 can vary between about 2.5 inches to about 5 inches (about 6.4 mm to about 12.7 mm) while the length $L_2$ can vary between from about 1 inch to about 2.5 inches (about 2.5 mm to about 6.4 mm). For best results, the ratio of $L_2/L_1$ should be between about 50 percent to about 80 percent, preferably the ratio of $L_2/L_1$ should be between about 60 percent to about 80 percent, and most preferably, the ratio of $L_2/L_1$ should be between from about 70 percent to about 75 percent. When one uses these ratios, one will obtain an absorbent article 74 where there will be an optical impression in the eyes of the viewer that the pair of flaps 104 and 106 are actually larger than their actual dimensions. This is beneficial for it allows the manufacturer to use a minimum amount of material while the consumer perceives the pair of flaps 104 and 106 to be larger and therefore providing better protection against staining of the undergarment.

Still referring to FIGS. 23 and 24, each of the flaps 104 and 106 includes an attachment means 114 and 116 for securing the pair of flaps 104 and 106 to one another. In FIGS. 23 and 24, the attachment means 116 is shown to be a patch of adhesive located on the outer surface of the flap 106 while the attachment means 118 is a patch of adhesive located on the inner surface of the flap 106. The flap 104 is designed to be folded around the undergarment first and then the second flap 106 is designed to be folded around the undergarment such that the adhesive 118 can contact adhesive 116 and the pair of flaps 104 and 106 can be held securely about the undergarment. It is also possible to make the flaps 104 and 106 shorter so that they do not overlap but instead have an attachment means 116 and 118 which are designed to be attached directly to the outer surface of the undergarment. When the flaps 104 and 106 are to be attached to the undergarment, the attachment means 116 and 118 are located on the inner surface of each flap 104 and 106. Besides the use of adhesives, the attachment means 116 and 118 can be a mechanical fastener such as a hook and loop type fastener. VELCRO™ is one type of hook and loop fastener. "VELCO" is a registered trademark of Velcro USA Inc. having an office at 406 Brown Ave,. Manchester, N.H. 03103. Other forms of fasteners include materials which will adhere to one another. For example, one could form the entire flap or a portion of each of the flaps, 104 and 106 respectively, out of a material that will adhere to another material. A cohesive-adhesive would cause the two flaps 104 and 106 to adhere to one another yet still be releasable. Still further, one could use a button and a mating button hole, a snap or some type of mechanical mechanism to hold the pair of flaps 104 and 106 together. All of these types of attachment means, as well as others known to those skilled in the art, are contemplated by this invention.

The absorbent article 74 further includes first and second channels 120 and 122 which are formed in the garment facing surface 98 of the pad 92. The first and second channels, 120 and 122 respectively, are sized and configured to mate with the side edges of an undergarment. A typical undergarment contains a waist opening and two leg openings with a crotch portion located between the two leg openings. The crotch portion normally contains a side edge or seam which continues about the periphery of each of the leg openings. The two side edges or seams are designed to contact the first and second channels, 120 and 122 respectively, as the undergarment is pulled up about the torso of the consumer. When the undergarment is in place, the side edges will enter the first and second channels, 120 and 122 respectively, and hold the absorbent article 74 secure against the body. By holding the absorbent article 74 close to or in contact with the body, one can minimize the amount of fluid leakage that may occur. This is very advantageous because if the body fluid drawn into the absorbent 90 instead of pooling up on the cover 86, one can substantially reduce the likelihood of leakage from occurring.

Referring again to FIG. 23, one will notice that the first and second raised longitudinally-extending sides, 78 and 80 respectively, do not extend the entire length of the absorbent article 74. Instead, the first and second longitudinally-extending sides, 78 and 80 respectively, extend along a substantial portion of the length of the absorbent article 74. By "substantial portion of the length" it is meant a distance which extends from between about 50 percent to about 95 percent of the length of the absorbent article 74. Preferably, the first and second longitudinally-extending sides, 78 and 80 respectively, extend a length of between about 60 percent to about 80 percent of length of absorbent article 74.

Turning again to FIG. 24, the outer surfaces 94 and 96 of the first and second longitudinally-extending sides, 78 and 80 respectively, have a height $H_1$ which can vary from between about 2 mm to about 25 mm. Preferably, the height $H_1$ is at least about 0.2 inches (about 5 mm), and more preferably, about 0.25 inches (about 6.4 mm). For thicker absorbent articles 74, the height $H_1$ should be about 0.5 inches (about 12.7 mm). Each of the raised longitudinally-extending sides, 78 and 80 respectively, has an inside height $H_2$ measured from the apex of each of the sides 78 and 80 to the body contacting surface 76. The height $H_2$ is less than $H_1$ and normally will be from between about 25 percent to about 75 percent less than the height $H_1$. Preferably, the height $H_2$ is at least about 50 percent less than the height $H_1$.

The height $H_1$ of the first and second raised longitudinally-extending sides, 78 and 80 respectively, should be sized and configured so as to at least partially, and preferably, fully enter the groins of the user. This will assure that the flaps 104 and 106 can only depend downward and inward from the outer surfaces 94 and 96. The flaps 104 and 106 will not be urged upwards by the undergarment.

Figure 25:
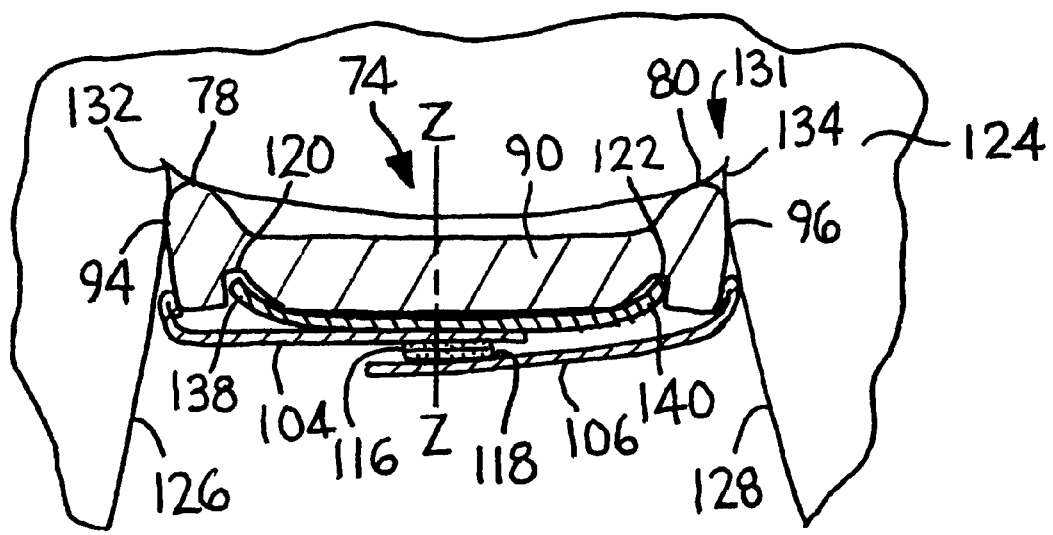
FIG. 25 is a cross-sectional view of a human torso with the absorbent article shown in FIG. 24 held secure against a body by an undergarment and having the pair of flaps wrapped around the crotch portion of the undergarment.

Referring now to FIG. 25, a human body is depicted having a torso 124 with a pair of thighs 126 and 128 depending therefrom. On the inside of each thigh 126 and 128 is a groin, 130 and 131 respectively, formed by the junction of the respective thigh 126 and 128 with the torso 124. Each of the groins 130 and 131 includes a crease, 132 and 134 respectively. The crotch portion of an undergarment 136 is depicted having two side edges or seams, 138 and 140 respectively, which form a portion of each of the leg openings in the undergarment 136. When the undergarment 136 is pulled up around the torso 124, the side edges 138 and 140 will enter, mate with or be received into the channels or groves 120 and 122 so as to hold the absorbent article 74 secure against the groins 130 and 131. The forces acting on the side edges 138 and 140 of the undergarment 136 will cause the first and second raised longitudinally-extending sides, 78 and 80 respectively, to enter the creases 132 and 134 respectively, and therefore, form a gasket with the body. This gasket will assure that fluid leakage is reduced when the absorbent article 74 is worn.

In FIG. 25, the absorbent 90 is shown without the cover 86 and the baffle 88. This is done solely for the purpose of clearly illustrating the absorbent article 74. The first and second raised longitudinally-extending sides 78 and 80 should be sized and configured so as to easily enter the groins 130 and 131. By this is meant that the height, width and length of the first and second raised longitudinally-extending sides, 78 and 80 respectively, will be configured so as to match up with the groins 130 and 131 of the consumer. The transverse spacing between the first raised side 78 and the second raised side 80 should be such that they will vertically register with the creases 132 and 134. It should be noted that the first and second raised longitudinally-extending sides, 78 and 80 respectively, do not have to fully enter the creases 132 and 134 of the groins, 130 and 131 respectively, but should at least partially enter into the creases 132 and 134. Because the anatomy of women does vary, it may be advantageous to configure the first and second raised longitudinally-extending sides, 78 and 80 respectively, to be linear for some products and to be non-linear for other products. For example, for the straight sided absorbent article 74 shown in FIG. 23, it may be advantageous to form the first and second raised longitudinally-extending sides, 78 and 80 respectively, to be linear while in an hourglass shaped absorbent article, the first and second raised longitudinally-extending sides, 78 and 80 respectively, may be non-linear or arcuate in shape.

When one carefully looks at FIG. 25, one will notice that the undergarment 136 is positioned adjacent to the absorbent article 74 and the pair of flaps 104 and 106 extend downwardly and inwardly so as to overlap one another. The pair of flaps 104 and 106 are attached to one another by the fasteners 116 and 118. In this position, the flaps 104 and 106 completely surround the crotch portion of the undergarment 136 and will prevent the undergarment, especially the edges 138 and 140 from becoming stained by body fluid.

Figure 26:
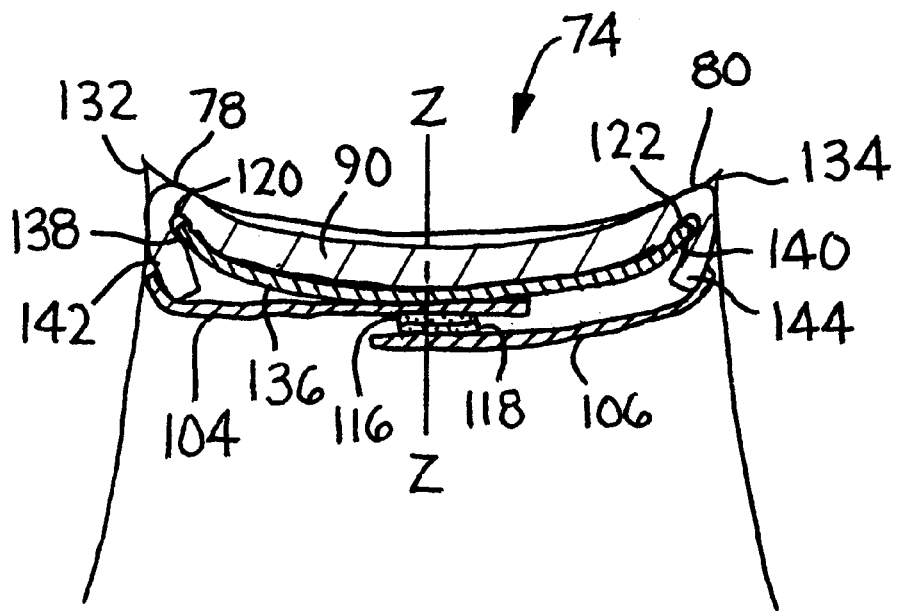
FIG. 26 is a cross-sectional view of an alternative embodiment of an absorbent article wherein the channels or grooves are located farther away from the central vertical axis z—z and the edges of the article depend down.

Referring now to FIG. 26, the absorbent article 74 is shown with the cover 86 and the baffle 88 removed so as to more clearly depict the raised sides 78 and 80 being engaged with the creases 132 and 134 of the groins 130 and 131 respectively. In this embodiment, the first and second channels, 120 and 122 respectively, are located further away from the vertical central axis z—z so that they are more vertically aligned with the creases 132 and 134. This embodiment allows for the distal side edges 142 and 144 of the absorbent 90 to extend downwardly and away from the creases 132 and 134. This downward orientation will cause the flaps 104 and 106 to move inward towards one another to a greater extent that that depicted in FIG. 25. However, as in FIG. 25, the flaps 104 and 106 do not extend upward but extend only downwardly and inwardly so as to wrap around and enclose the undergarment 136. It should be noted that the distance between the channels 120 and 122 can vary but a distance of between about 2 inches to about 4 inches (about 51 mm to about 102 mm) will work. A more preferred distance between the channels 120 and 122 is between about 2 inches to about 3 inches (about 51 mm to about 76 mm).

Figure 27:
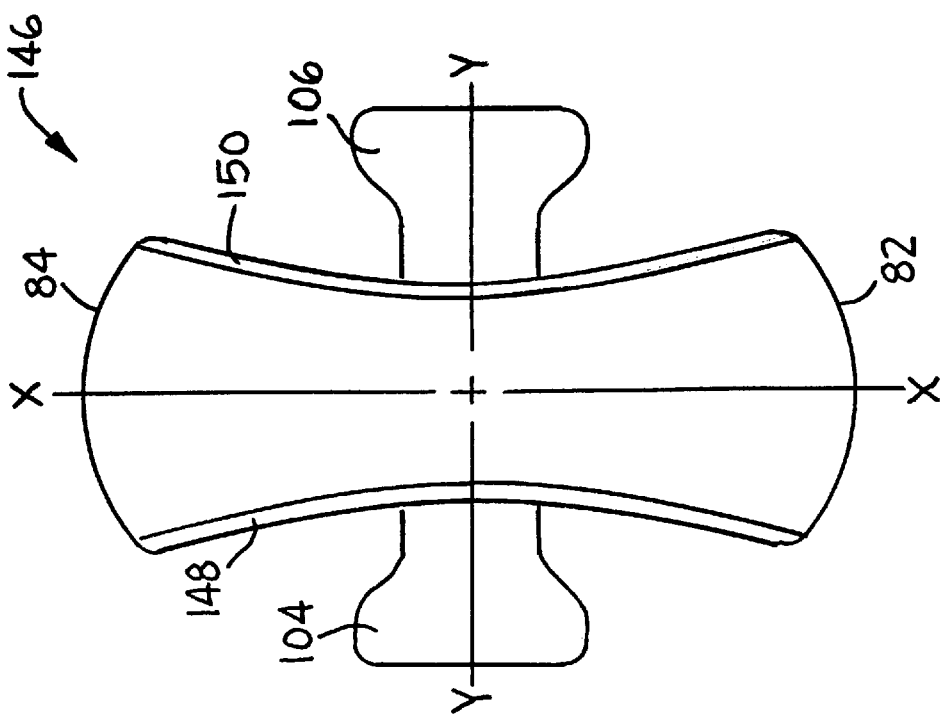
FIG. 27 is a top view of an absorbent article having an hourglass shape and the pair of raised longitudinally-extending sides extend along essentially the entire length of the article.

Referring to FIG. 27, an alternative embodiment of an absorbent article 146 is shown having an hourglass configuration. The hourglass configuration has a first raised longitudinally-extending side 148 and a second raised longitudinally-extending side 150. Each of these raised sides 148 and 150 is non-linear in appearance. Because of this, the first and second raised longitudinally-extending sides, 148 and 150 respectively, are arranged close together at the transverse centerline y—y and are spaced apart at a greater distance approximate the ends 82 and 84. Each of the first and second raised longitudinally-extending sides, 148 and 150 respectively, also extends essentially the entire length of the absorbent article 146. In a typical hourglass configuration, the raised sides 148 and 150 can have an arcuate or curved configuration.

Figure 28:
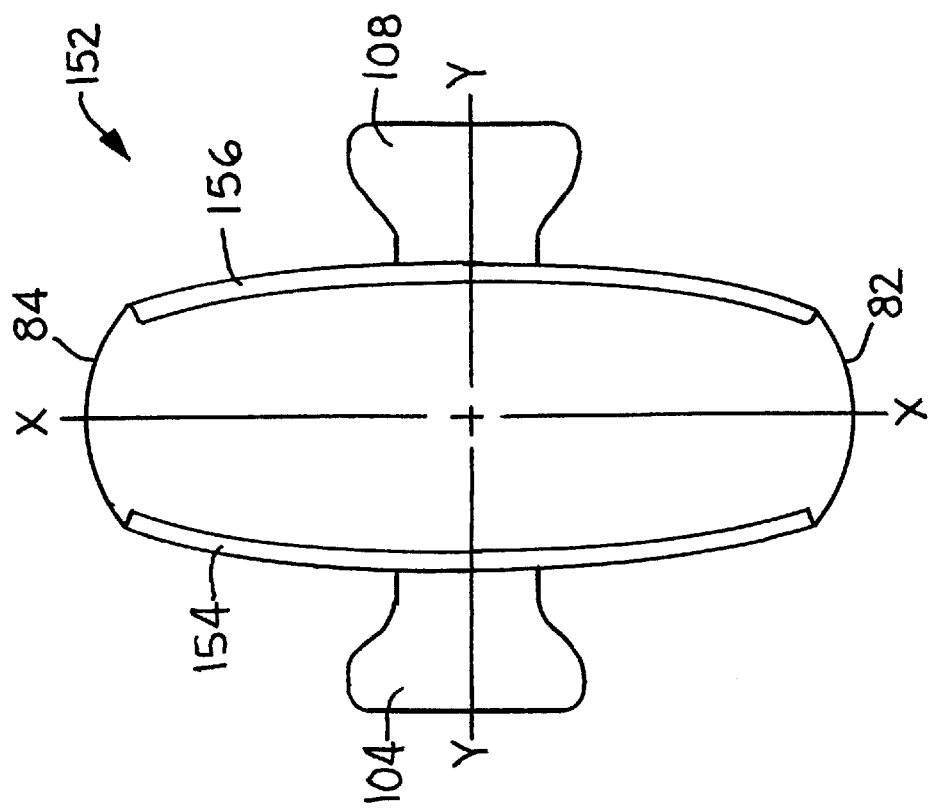
FIG. 28 is a top view of an absorbent article having a generally oval shape and the pair of raised longitudinally-extending sides are arcuate in configuration.

Referring to FIG. 28, still another embodiment of an absorbent article 152 is shown having an oval shape. The absorbent article 152 contains a first raised longitudinally-extending side 154 and a second raised longitudinally-extending side 156. The two raised longitudinally-extending sides 154 and 156 are curved or non-linear in configuration and extend over a length which is slightly less than the overall length of the absorbent article 152. The first and second raised longitudinally-extending sides, 154 and 156 respectively, are spaced farther apart at the transverse centerline y—y and are spaced closer together approximate the ends 82 and 84. The difference in size, configuration and position of the first and second raised longitudinally-extending sides 148 and 150, and 154 and 156 will allow a manufacturer to produce absorbent articles which will best fit the anatomy of a number of different woman. Some woman may prefer the hourglass shaped absorbent article 146, while others may prefer the oval shaped absorbent article 152, while still others may prefer the more rectangular shaped absorbent article 74.

Figure 29:
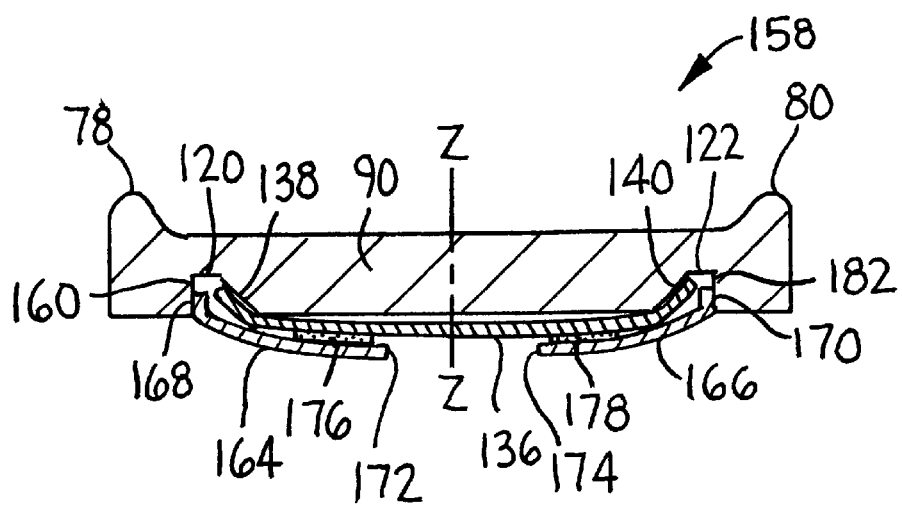
FIG. 29 is a cross-sectional view of an absorbent article having a pair of flaps which are secured to a surface of the first and second channels, respectively, and which do not overlap one another.
Figure 30:
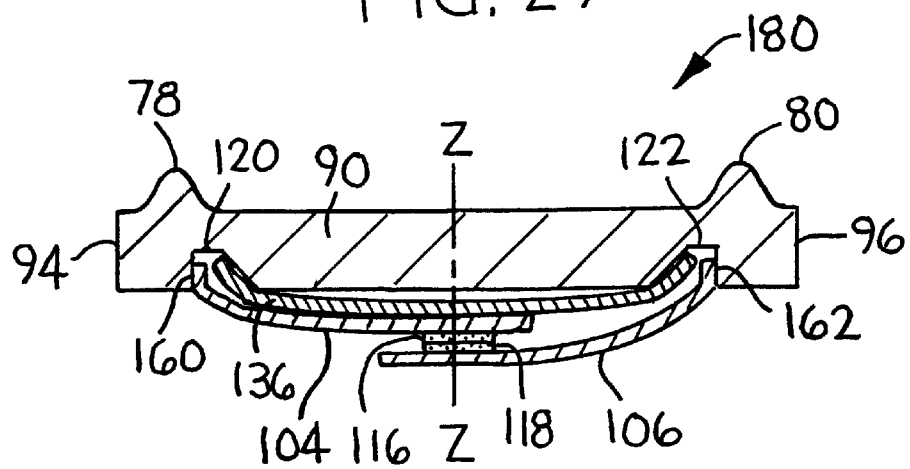
FIG. 30 is a cross-sectional view of an absorbent article having a pair of flaps which are secured to a surface of the first and second channels, respectively and which are designed to overlap one another.
Figure 31:
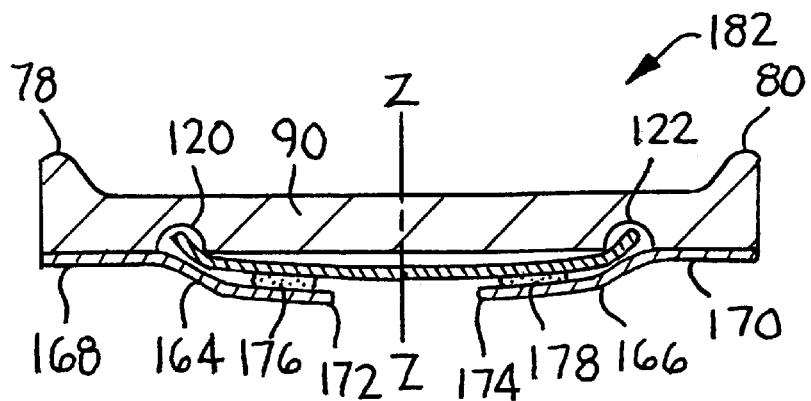
FIG. 31 is a cross-sectional view of an absorbent article having a pair of flaps which are secured to a lower surface of the absorbent article and which do not overlap one another.

Referring now to FIGS. 29–31, three additional embodiments are depicted. In FIG. 29, an absorbent article 158 is shown with the cover 86 and the baffle 88 removed so as to more clearly depict the undergarment 136 entering the channels 120 and 122. Each of the channels 120 and 122 has an interior wall, 160 and 162 respectively, onto which is secured a flap 164 and 166 respectively. Each of the flaps 164 and 166 has a proximal edge, 168 and 170 respectively, and a distal edge, 172 and 174 respectively. The proximal edges 168 and 170 are designed to be secured to the interior wall 160 and 162 of each of the channels 120 and 122. Each of the flaps 164 and 166 also has an attachment means , such as a spot or patch of adhesive or a mechanical fastener which is designed to be secured to the lower surface of the undergarment 136. The flaps 164 and 166 do not overlap one another but instead are sized and configured to extend downwardly and inwardly around a portion of the undergarment 136 and be attached directly to the undergarment.

One unique benefit of having the flaps 164 and 166 being attached to a surface of the channels 120 and 122 is that the first and second raised longitudinally-extending sides 78 and 80 can enter the creases of the groin and will not be biased downward by the attachment of the flaps 164 and 166 to the undergarment 136. Another advantage of this design is that the absorbent 90 can be made as wide as needed while the flaps 164 and 166 can be reduced in size. Since the flaps 164 and 166 extend downward and inward from the channels 120 and 122 instead of the outside side edges of the absorbent 90. A third advantage of having the flaps 164 and 166 extend downward from the channels 120 and 122 is that they assist in keeping the side edges 138 and 140 of the undergarment 136 in place. With the flaps 164 and 166 being secured as shown in FIG. 29, the undergarment 136 can not easily move outward away from the channels 120 and 122.

Referring now to FIG. 30, an absorbent article 180 is shown which differs from the embodiment shown in FIG. 29 in two noticeable ways. First, the pair of flaps 104 and 106 are designed to overlap one another and be connected together by the attachment means 116 and 118. Second, the first and second raised longitudinally-extending sides, 78 and 80 respectively, are located inward from the vertical outer surfaces 94 and 96. The closer arrangement of the first and second raised longitudinally-extending sides, 78 and 80 respectively, will allow the absorbent article 180 to better fit woman with narrower groin spacing. Again, the attachment of the flaps 104 and 106 to the walls 160 and 162 of the channels, 120 and 122 respectively, will assist in holding the undergarment 136 in place.

Lastly, referring to FIG. 31, an absorbent article 182 is shown having a pair of flaps 164 and 166. Each flap 164 and 166 has a proximal edge, 168 and 170 respectively, and a distal edge, 172 and 174 respectively. The difference between the embodiment shown in FIG. 31 and the embodiment shown in FIG. 29 is that in FIG. 31 the flaps 164 and 166 are attached to a lower surface of the absorbent article 182 approximate their proximal edges 168 and 170. The flaps 164 and 166 are secured such that they extend inward toward the vertical centerline z—z. The flaps are sized and configured so as not to overlap one another. Each of the flaps 164 and 166 has an attachment means, 176 and 178 respectively, such as adhesive, which is used to releaseably secure the flaps 164 and 166 to the undergarment 136. It should be noted that it may be easier to attach the flaps 164 and 166 to the lower surface of the absorbent article, as depicted in FIG. 31, than trying to attach them the interior surface of each of the channels 120 and 122.

While the invention has been described in conjunction with a specific embodiment, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

We claim:

1. An absorbent article designed to be secured to an undergarment, the undergarment having a crotch portion with a pair of side edges, the absorbent article comprising:
   a) a liquid permeable cover;
   b) a liquid-impermeable baffle;
   c) an absorbent enclosed by the cover and the baffle to form a pad, the pad having first and second raised longitudinally-extending sides and a garment-facing surface;
   d) first and second channels formed in the garment-facing surface of the pad, the first and second channels being sized and configured to mate with the side edges of the undergarment;
   e) a pair of flaps sized to depend downwardly and inwardly around the crotch portion of the undergarment so as to prevent staining of the undergarment by any body fluid, each of the flaps having a distal edge and a proximal edge, wherein the proximal edge is affixed to one of the channels, the proximal edge of each flap having a length $L_2$ and the distal edge of each flap having a length $L_1$, the ratio of $L_2/L_1$ being between about 50 to about 80 percent; and
   f) attachment means for securing the pair of flaps to the undergarment.

2. The absorbent article of claim 1, wherein the proximal edge of each flap has a length $L_2$ and the distal edge of each flap has a length $L_1$, and the ratio of $L_2/L_1$ is between about 60 to about 80 percent.

3. The absorbent article of claim 1, wherein the proximal edge of each flap has a length $L_2$ and the distal edge of each flap has a length $L_1$, and the ratio of $L_2/L_1$ is between about 70 to about 75 percent.

4. An absorbent article designed to be secured to an undergarment, the undergarment having a crotch portion with a pair of side edges, the absorbent article comprising:
   a) a liquid permeable cover;
   b) a liquid-impermeable baffle;
   c) an absorbent enclosed by the cover and the baffle to form a pad, the pad having first and second raised longitudinally-extending sides and a garment-facing surface;
   d) first and second channels formed in the garment-facing surface of the pad, the first and second channels being sized and configured to mate with the side edges of the undergarment;
   e) a pair of flaps sized to depend downwardly and inwardly around the crotch portion of the undergarment so as to prevent staining of the undergarment by any body fluid, each of the flaps having a distal edge and a proximal edge, wherein the proximal edge is affixed to one of the channels, the proximal edge of each flap having a length $L_2$ and the distal edge of each flap having a length $L_1$, the ratio of $L_2/L_1$ being between about 50 to about 80 percent; and
   f) attachment means for securing the pair of flaps to one another.

5. The absorbent article of claim 4, wherein the proximal edge of each flap has a length $L_2$ and the distal edge of each flap has a length $L_1$ and the ratio of $L_2/L_1$ is between about 60 to about 80 percent.

6. The absorbent article of claim 4, wherein the proximal edge of each flap has a length $L_2$ and the distal edge of each flap has a length $L_1$, and the ratio of $L_2/L_1$ is between about 70 to about 75 percent.

* * * * *